United States Patent
Branstrom et al.

(10) Patent No.: US 7,235,234 B1
(45) Date of Patent: Jun. 26, 2007

(54) BACTERIAL DELIVERY SYSTEM

(75) Inventors: Arthur A. Branstrom, Rockville, MD (US); Donata R. Sizemore, Gaithersburg, MD (US); Jerald C. Sadoff, Washington, DC (US)

(73) Assignee: United States of America as Represented by the Secretary of the Army, Washington, DC (US)

( * ) Notice: Subject to any disclaimer, the term of this patent is extended or adjusted under 35 U.S.C. 154(b) by 267 days.

(21) Appl. No.: 09/512,810

(22) Filed: Feb. 25, 2000

Related U.S. Application Data

(63) Continuation of application No. 08/711,961, filed on Sep. 6, 1996, now Pat. No. 7,045,336.

(60) Provisional application No. 60/018,035, filed on May 21, 1996, provisional application No. 60/003,318, filed on Sep. 6, 1995.

(51) Int. Cl.
    *C12N 1/20* (2006.01)
(52) U.S. Cl. .................. 424/93.2; 424/93.4; 435/252.3
(58) Field of Classification Search ............ 435/252.1, 435/245, 252.3; 424/93.2, 93.21, 93.4
    See application file for complete search history.

(56) References Cited

U.S. PATENT DOCUMENTS

| | | | |
|---|---|---|---|
| 3,891,751 A | 6/1975 | Pilet et al. | |
| 4,888,170 A | 12/1989 | Curtiss, III | |
| 5,077,044 A | 12/1991 | Stocker | |
| 5,112,749 A | 5/1992 | Brey, III et al. | |
| 5,468,485 A | 11/1995 | Curtiss, III | |
| 5,672,345 A | 9/1997 | Curtiss, III | |
| 5,824,538 A | 10/1998 | Branstrom et al. | |
| 5,877,159 A | 3/1999 | Powell et al. | |
| 6,410,012 B1* | 6/2002 | Sizemore et al. | 424/93.2 |
| 6,531,313 B1* | 3/2003 | Goudsmit et al. | 435/320.1 |

FOREIGN PATENT DOCUMENTS

EP  0211543  2/1987

OTHER PUBLICATIONS

Zabner et al, "Cellular and molecular barriers to gene transfer by cationic lipid." J Biol Chem, Aug. 1995, 270 (32): 18997-19007 abstract.

Higgins et al. "Bacterial delivery of DNA evolves", Nature Biotechnology, Feb. 1998, 16:138-139.

Zychlinsky et al, "IpaB mediates macrophage apoptosis induced by *Shigella flexneri*." Mol Microbiol, 1994, 11 (4): 619-627 abstract.

(Continued)

*Primary Examiner*—James Ketter
(74) *Attorney, Agent, or Firm*—Elizabeth Arwine; Charles H. Harris

(57) ABSTRACT

We describe a bacterial delivery system for the delivery of DNA and antigens into cells. We constructed an attenuated bacterial vector which enters mammalian cells and ruptures delivering functional plasmid DNA and antigens into the cell cytoplasm. This *Shigella* vector was designed to deliver DNA to colonic surfaces, thus opening the possibility of oral and other mucosal DNA immunization and gene therapy strategies. The attenuated *Shigella* is also useful as a vaccine for reducing disease symptoms caused by *Shigella*.

4 Claims, 7 Drawing Sheets

OTHER PUBLICATIONS

Zychlinksy et al, "Molecular and cellular mechanisms of tissue invasion by *Shigella flexneri*." Ann NY Acad Sci, 1994, 730: 197-208.

Galan et al. "Cloning and characterization of the *asd* gene of *Salmonella typhimurium*: use in stable maintenance of recombinant plasmids in *salmonella* vaccine strains", Gene, 1990, 94-35.

Hatten et al. "Cloning and characterization of the *Neisserian menigitidis* asd gene", , Gene, 1993, 129: 123-128.

Slauch et al. "In Vivo Expression Technology for Selection of Bacterial Genes Specifically Induced in Host Tissues", Methods In Enzymology, 1994, 235: 481-492.

Powell et al, "Introduction of Eukaryotic expression cassettes into animal cells using a bacterial vector delivery system." Vaccines, 1996, 183 abstract.

Donnelly et al. Immunization with DNA. *J. Immun. Methods*, 1994, 176: 145-152.

El-Hajj et al. "Lethality of a *dut* (Deoxyuridine Triphosphatese) Mutation in *Escherichia coli*", Journal of Bacterilogy, 1988, 170(3): 1069-1075.

High et al. "IpaB of *Shigella flexneri* causes entry into epitelial cells and escape form the phagocytic vacuole", The EMBO Journal, 1992, 11(5): 1991-1999.

Oyston et al. "Immunization with Live Recombinant *Salmonella typhimurium aroA* Producing F1 Antigen Protects against Plague", Infection and Immunity, Feb. 1995, 63(2): 563-568.

Formal et al. "Genetic Transfer of *Shigella flexneri* Antigens to *Escherichia coli* K-12[1]" Infection and Immunity, Mar. 1970, 1(3):279-287.

Sansonetti et al. "Alterations in the Pathogenicity of *Escherichia coli* K-12 After Transfer of Plasmid and Chromosomal Genes from *Shigella Flexneri*", Infection and Immunity, Mar. 1983, 39(3): 1392-1402.

Formal et al. "Oral Vaccination of Monkeys with an Invasive *Escherichia coli* K-12 Hybrid Expressing *Shigella Flexneri* 2a Somatic Antigen", Infection and Immunity, Nov. 1984, 46(2): 462-469.

Newland et al. "Genotypic and phenotypic characterization of an *aroD* deletion-attenuated *Escherichia coli* K12-*Shigella Flexneri* hybrid vaccine expressing *S. flexneri* 2a somatic antigen", Vaccine, 1992 10(11): 766-776.

Portnoy et al. "The Cell Biology of *Listeria monocytogenes* Infection (Escape from a Vacuole)", Annals New York Academy of Sciences, Aug. 15, 1994, 730: 15-25.

Kadurugamuwa et al. "Intercellular Spread of *Shigella flexneri* through a Monolayer Mediated by Membranous Protrusions and Associated with Reorganization of the Cytoskeletal Protein Vinculin", Infection and Immunity, Oct. 1991, 59(10): 3463-3471.

Lawlor et al. "Virulence of Iron Transport Mutants of *Shigella flexneri* and Utilization of Host Iron Compounds", Infection and Immunity, Mar. 1987, 55(3): 594-599.

Vasselon et al. "Stress Fiber-Based Movement of *Shigella flexneri* within Cells", Infection and Immunity, May 1991, 59(5): 1723-1732.

Barrow et al. "Contribution of *Salmonella gallinarum* Large Plasmid toward Virulence in Fowl Typhoid" , Infection and Immunity, Feb. 1987, 55(2): 388-392.

Barrow et al. "Host Specificity of *Salmonella* Infection in Chickens and Mice Is Expressed In Vivo Primarily at the Level of the Reticuloendothelial System", Infection and Immunity, Oct. 1994, 62(10): 4602-4610.

Keller et al. "*Salmonella enteritidis* Colonization of the Reproductive Tract and Forming and Freshly Laid Eggs of Chicken", Infection and Immunity, Jul. 1995, 63(7): 2443-2449.

Hassan et al. "Virulent *Salmonella typhimurium*-Induced Lymphocyte Depletion and Immunosuppression in Chickens", Infect. and Immun., May 1994, 62(5):2027-2036.

Cardenas et al. "Stability, immunogencity and expression of foreign antigens in bacterial vaccine vectors", Vaccine, 1993, 11(2): 126-135.

Cirillo et al. "Bacterial Vaccine Vectors and *Bacullus calmette-guerin*", Clinical Infectious Diseases, 1995, 20: 1001-1009.

Sizemore et al. "Attenuated *Shigella* as a DNA Delivery Vehicle for DNA-Mediated Immunization", Science, Oct. 13, 1995, 270:289-302.

Aggarwal et al, "Oral *Salmonella*: Malaria Circumsporozoite Recombinants Induce Specific CD8+ Cytotoxic T Cells", J. Exp. Med., 1990, 172(4):1083-1090.

Noriega et al. "Construction and Characterization of Attenuated ΔaroAΔ ΔvirG *Shigella flexneri* 2a Strain CVD 1203, a Prototype Live Oral Vaccine", Infection and Immunity, Nov. 1994, 62(11): 5168-5172.

Cory et al, "Characterization of a Messenger RNA Polynucleotice Vaccine Vector[1]", Cancer Research, Apr. 1, 1995, 55: 1397-1400.

Ulmer et al, "Heterologous Protection Against Influenza by Injection of DNA Encoding a Viral Protein", Mar. 19, 1993, 259: 1745-1749. Mar. 19, 1993, 259: 1745-1749.

Wolff et al, "Direct Gene Transfer into Mouse Muscle In Vivo", Science, Mar. 23, 1990, 247:1465-1468.

Gillies et al. "A Tissue-Specific Transcription Enhancer Element is located in the Major Intron of a Rearranged Immunoglobulin Heavy Chain Gene", Cell, 33:717-728 (1983).

Sandri-Goldin et al. "High-Frequency Transfer of Cloned Herpes Simplex Virus Type 1 Sequence to Mammalian Cells by Protoplast Fusion", Mol. Cell. Biol., Aug. 1981, 1(8):743-752.

Schaffner et al. "Direct Transfer of Cloned Genes from Bacteria to Mammalian Cells", Proc. Nat; Acad. Sci. USA, 1988, 77(4):2163-2167.

Van De Verg et al. Antibody and cytokine responses in a mouse pulmonary model of *Shigella flexneri* serotype 2a infection. Infection and Immunity, 1995, 63: 1947-1954.

Sun et al. Cholera toxin B subunit: an efficient transmucosal carrier-delivery system for induction of peripheral immunological tolerance. PNAS, 1994, 91: 10795-10799.

ASM Meeting News, 95th General Meeting, Washington, DC May 23, 1995. Mucosal surfaces present a new vaccine approach.

Zychlinsky et al. "*Shigella flexneri* induces apoptosis in infected macrophages", Nature, 1992, 358:167-169.

Hartman et al. "Small -animal model to measure efficacy and immunogenicity of *Shigella* vaccine strains", Infection and Immunity, 1991, 59: 4075-4083.

Oaks et al. "Plaque formation by virulent *Shigella flexneri*", Infection and Immunity, 1985, 48:124-129.

Mills et al. *Shigella flexneri* invasion plasmid antigens B and C: epitope location and characterization with monoclonal antibodies. *Infection and Immunity*, 1998, 56:2933-2941.

Hartman et al. Local immune response and protection in the guinea pig keratoconjunctivitis model following immunization with *Shigella* vaccines. Infection and Immunity, 1998, 62: 412-420.

Steiner et al. "The Missing Link in Phage Lysis of Gram-Positive Bacteria: Gen 14 of *Bacullus subtilis* Phage sym29 Encodes the Functional Homology of Lambda S Protein", Journal of Bacteriology, 1993, 175(4): 1038-1042.

Nakayama et al. Construction of an ASD+ expression-cloning vector; stable maintenance and high level expression of cloned genes in a *Salmonella* vaccine strain. Bio/Technology, 1988, 6: 693-697.

Pascual et al. "Oral Bacterial Vaccine Vectors for the Delivery of Subunit and Nucleic Acid Vaccines to the Organized Lymphoid Tissue of the Intestine", Behring Inst. Mitt., 1997, 98: 143-152.

Branstom, Arthur A. "Stable plasmid maintenance of HIV genes in *S. typhimurium* and *S. typhi*", Presented at the 33rd ICAAC, New Orleans, LA, Oct. 20, 1993, Abstract #102888.

Fouts et al. "Construction and characterization of a *Salmonella typhi*-based human immunodefiency virus type 1 vector Vaccine", Vaccine, 1995, 13(6): 561-569.

Yoshikawa et al. "Construction and evaluation of a *virG thyA* double mutant of *Shigella flexneri* 2a as candidate live- attenuated oral vaccine", Vaccine, 1995, 13(15) 1436-1440.

Sandlin et al. "Avirulence of Rough Mutans of *Shigella flexneri*: Requirement of O Antigen for Correct Unipolar Localization of IcsA in the Bacterial Outer Membrane", Infection and Immunity, 1995, 63(1): 229-237.

Darji et al. "Oral Somatic Transgene Vaccination Using Attenuated *S. typhimurium*", Cell, 1997, 91: 765-775.

Karow et al. "Isolation and Characterization of the *Escherichia coli htrB* Gene, Whose Product Is Essential for Bacterial Viability above 33C i Rich Media", Journal of Bacteriology, 1991,173(2): 741-750.

Lipinska et al. "The htrA (DegP) Protein, Essential for *Escherichia coli* Survival at High Temperatures, Is an Endopeptidase", Journal of Bacteriology, 1990, 172(4): 1791-1797.

Baumler et al. "*Salmonella typhimurium* Loci Involved in Survival within Macrophages", Infection and Immunity, May 1994, 62(5): 1623-1630.

Johnson et al. "The role of a stress-response protein in *Salmonella typhimurium* virulence", Molecular Microbiology, 1991, 5(2): 401-407.

Dolly Aggarwal Parasrampuria "Therapeutic Delivery Issues in Gene Therapy, Part 1 Vectors", BioPharm, Mar. 1998, 38-44.

Dolly Aggarwal Parasrampuria "Therapeutic Delivery Issues in Gene Therapy, Part 2 Targeting Approaches", BioPharm, Mar. 1998, 58-66.

Dietrich et al. "Delivery of antigen-encoding plasmid DNA into the cytosol of macrophages by attenuated suicide *Listeria monocytogenes*", Nature Biotechnology, Jan. 1998, 16: 181-185.

John Travis, "Swallowing Shigella can bacteria that cause food poisoning deliver oral DNA vaccines?" Science News, May 1996, 149:302-303.

Allsopp et al., "Comparison of numerous delivery systems for the induction of Cytotoxic T Lymphocytes by Immunization." Eur J Immunol, Aug. 1996, 26 (8): 1951-1959 abstract.

Anderson et al., "Gene expression in rainbow trout (*Oncorhynchus mykiss*) following Intramuscular injection of DNA." Mol Mar Biol Biotechnol, Jun. 1996, 5(2): 105-113 abstract.

Bellon et al, "Aerosol administration of a recombinant adenovirus expressing CFTR to Cyctic fibrosis patients: a phase I clinical trial." Hum Gene Ther, Jan. 1997, 8(1): 15-25 abstract.

Bielecki et al., "*Bacillus ubtilis* expressing a haemolysin gene from Listeria Monocytogenes can grow in mammalian cells." Nature, May 1990, 345 (6271): 175-176 abstract.

Bourne et al. "DNA immunization against experimental genital herpes simplex virus infection." J Infect Dis, Apr. 1996, 173 (4): 800-807 abstract.

Boyer et al., "In vivo protective anti-HIV immune responses in non-human primates Through DNA immunization." J Med Primatol, Jun. 1996, 25(3): 242-250 abstract.

Brehm et al., "Regulation of virulence gene expression pathogenic Listeria." Microbiologia, 1996, 12 (2): 219-236 abstract.

Cirillo et al., "Identification of a domain in Rck, a product of the *Salmonella typhmurium* Virulence plasmid, required for both serum resistance and cell invasion." Infect Immun 1996, 64(6): 2019-2023 abstract.

Citovsky et al., "Transport of nucleic acids through membrane channels: snaking Through small holes." Annu. Rev. Microbiol, 1993, 47: 167-197 abstract.

Collas, et al., "The nuclear localization sequences of the SV40 T antigen promotes Transgene uptake and expression in zerbrafish embryo nuclei." Transgenic Res Nov. 1996, 5 (6): 451-458 abstract.

Courvalin et al., "Gene transfer from bacteria to mammalian cells." C R Acad Sci III Dec. 1995, 318 (12): 1207-1212 abstract.

Davis, et al., "DNA vaccine for hepatitis B: evidence for immunogenicity in Chimpanzees and comparison with other vaccines." Proc Natl Acad Sci USA Jul. 1996, 93 (14): 7213-7218 abstract.

Donnelly, et al., "Preclinical efficacy of a prototype DNA vaccine: enhanced protection against antigenic drift in influenza virus." Nat Med Jun. 1995, 1(6):583-587 abstract.

Dowty et al., "Plasmid DNA entry into postmitotic nuclei of primary rat myotubes." Proc Natl Acad Sci USA, 1995, 92(10): 4572-4576 abstract.

Elsinghorst et al., "Molecular cloning of epithelial cell invasion determinats from Enterotoxigenic *Escherichia coli.*" Infect Immun, Jun. 1992, 60 (6): 2409-2417 abstract.

Finaly et al., "Comparison of the invasion strategies used by *Salmonella cholerae-Suis, Shigella flexneri* and *Yersinia enterocolitica* to enter cultured animal cells: Endosome acidification is not required for bacterial invasion or intracellular replication" Biochimie, 1988, 70(8): 1089-1099 abstract.

Fleszig et al., "Relationship between cytotoxicity and corneal epithelial cell invasion By clinical isolates of *Pseudomonas aeruginosa.*" Infect Immun, 1996, 64 (6): 2288-2294 abstract.

Fletcher et al., "Novel invasion determinate of enteropathogenic *Escherichia coli* Plasmid pLV501 encodes the ability to invade intestinal epithelial cells and Hep-2 Cells." Infect Immun, 1992, 60 (6): 2229-2236.

Freitag et al., "Transcriptional activation of the Listeria moncytogenes hemolysin gene In *Bacullus subtills.*" J. Bacteriol, Feb. 1992, 174 (4): 1293-1298 abstract.

Fynan et al., "Use of DNA encoding influenza hemagglutinin as an avian influenza Vaccine." DNA Cell Biol, Nov. 1993, 12(9): 785-789 abstract.

Fynan et al., "DNA vaccines: protective immunizations by parenteral, mucosal, and Gene-gun inoculations." Proc Natl Acad Sci USA, Dec. 1993, 90 (24): 11478-11482 abstract.

Fynan et al., "DNA vaccines: a novel approach to immunization." Int J Immunophar-Macol, Feb. 1995, 17 (2): 79-83, abstract.

Gaillard et al., "The in1AB locus mediates the entry of Listeria monoctogenes into Hepatocytes in vivo." J Exp Med, 1996, 183(2):359-369, abstract.

Galan., "Cloning and characterization of the asd gene of *Salmonella typhimurium*: In stable maintenance of recombinant plasmids in *Salmonella* vaccine strains." Gene, 1990, 94 (1): 29-35. abstract use.

Graessmann et al., "Helper activity for gene expression, a novel function of the SV40 Enhancer." Nucleic Acids Res, 1989, 17 (16): 6603-6612, abstract.

Greco et al., "Invasion of cultured human cells by *Streptococcus pyogenes.*" Res Microbiol, 1995, 146(7): 551-560 abstract.

Hanski et al., "Determinants of invasion and survival of *Yersinia enterocolitica* in Intestinal tissue. An in vivo study." Med Microbiol Immunol, 1989, 178 (5): 289-296 abstract.

Henrich et al., "Primary structure and functional analysis of the lysis genes of *Lactobacillus gasseri* bacteriophage phi adh." J Bacteriol, 1995, 177 (3): 723-732 abstract.

Hess et al., "Listeria monocytogenes p60 supports host cell invasion by and in vivo Survival of attentuated *Salmonella typhimurium.*" Infect Immun, 1995, 63 (5): 2047-2053 abstract.

Hoang et al., "Molecular genetic analysis of the region containing the essential *Pseudomanas aeruginosa* asd gene encoding aspartate-beta-semialdehyde Dehydrogenase." Microbiology, 1997, 143(pt3): 899-907 abstract.

Hoffman et al., "Nucleic acid malaria vaccines. Current status and potential." Ann NY Acad Sci, Nov. 1995, 772: 88-94 abstract.

Huang et al., "*Escherichia coli* invasion of brain microvascular endothelial cells in Vitro and in vivo: molecular cloning and characterization of invasion gene ibe10." Infect Immun, Nov. 1995, 63(11): 4470-4475 abstract.

Jones S, Portnoy, "Characterization of *Listeria* monocytogenes pathogenesis in a strain expressing perfringolysin O in place of listerioysin O." Infect Immun, 1994, 62 (12): 5608-5613 abstract.

Jones et al., "Conversion of an extracellular cytolysin into a phagosome-specific lysin which supports the growth of an intracellular pathogen", Mol Micribiol, 1996, 21(6): 1219-1226 abstract.

Karunasagar et al., "Complementation of *Listeria seeligeri* with the plcA-prfA genes from L. monocytogenes activates transcription of seeligerolysin and leads to bacterial escapes from the phagosome of infected mammalian cells." FEMS Microbiol Lett, Jan. 1997, 146(2): 303-310 abstract.

Keller et al., "In vivo particle-mediated cytokine gene transfer into canine oral mucosa and epidermis." Cancer Gene Ther, May 1996, 3 (3): 186-191 abstract.

Kusters et al., "Effects of multiplicity of infection, bacterial protein synthesis, and growth phase on adhesion to and invasion of human cell lines by *Salmonella typhimurium.*" Infect. Immun, 1993, 61 (12): 5013-5020 abstract.

Labar-Moleur et al., "An electron microscopy study into the mechanism of gene transfer with lipopolyamines." Gene Ther, 1996, 3(11): 1010-1017 abstract.

Lu S et al., "Simian immunodeficiency virus DNA vaccine trial in macaques." J Virol, Jun. 1996, 70 (6): 3978-3991 abstract.

Mahvi et al. "Particle-mediated gene transfer of granulocyte-macrophage colony-stimulating factor cDNA to tumor cells: implications for a clinically relevant tumor vaccine." Hum Gene Ther, Aug. 1996, 7 (13): 1535-1543 abstract.

Miliotis et al. "Adherence to and invasion of tissue culture cells by i Vibrio hollisae." Infect Immun, 1995, 63(12): 4959-4963 abstract.

Miller, VL, "Tissue-culture invasion: fact or artefact?" Trends Microbiol, Feb. 1995, 3(2): 69-71 abstract.

Monteil et al, "Genetic immunization of seronegative one-day-old piglets against pseudorabies induces neutralizing antibodies but not protection and is ineffective in piglets from immune dams." Vet Res, 1996, 27(4-5): 443-452 absract.

Naghton et al., "A rat model of infection by *Salmonella typhimurium* or *Salm. enteritidis*." J. Appl Bacteriol, 1996, 81(6): 651-656 abstract.

Oelschllaeger et al., "Some structures and processes of human epithelial cells involved in uptake of enterohemorrhagic *Escherichia coli* O157:H7 strains." Infect Immun, 1994, 62(11): 5142-5150 abstract.

Okuda et al., "Induction of potent humoral and cell-mediated immune responses following direct injection of DNA encoding the HIV type 1 env and rev gene products." Aids Res Hum Retroviruses, Aug. 1995, 11(8): 933-943 abstract.

Pepe et al., *Yersinia enterocolitica* invasion: a primary role in the initiation of infection. Proc Natl Acad Sci USA, Jul. 1993, 90 (14): 6473-6477 abstract.

Portnoy et al., "Capacity of listeriolysin O, streptolysin O, and perfringolysin O to mediate growth of *Bacillus subtilis* within mammalian cells." Infect Immun, 1992, 60 (7): 2710-2717 abstract.

Rakhmilevich et al., "Gene gun-mediated skin transfection with interleukin 12 gene results in regression of established primary and metastic murine tumors." Proc Natl Acad Sci USA, Jun. 1996, 93 (13): 6291-6296 abstract.

Raz et al., "Modulation of disease activity in murine systemic lupus erythematosus by cytokine gene delivery." Lupus, Aug. 1995, 4 (4): 286-292 abstract.

Robinson et al., "Protection against a lethal influenza virus challenge by immuniza-tion with a haemagglutinin-expressing plasmid DNA." Vaccine, 1993, 11 (9): 957-960 abstract.

Schmidt et al., "Three functions of bacteriophage P1 involved in cell lysis." J Bacteriol, 1996, 178 (4): 1099-1104 abstract.

Sedagah et al., "Protection against malaria by immunzation with plasmid DNA encoding cirumsporozoite protein." Proc Natl Acad Sci USA, Oct. 1994, 91 (21): 9866-9870 abstract.

Shaw, D, "Human tests on a vaccine to stop AIDS" Philadelphia Inquirer, Mar. 25, 1996, C01.

Stocker et al., "Aromatic-dependent "*Salmonella sp.*" as live vaccine in mice and calves." Dev Biol Stand, 1983, 53: 47-54 abstract.

Teysseire et al., "*Rickettsia conorii* entry into Vero cells." Infect Immun, 1995, 63 (1): 366-374 abstract.

Thorsness et al., "Escape and mirgration of nucleic acids between chloroplasts, mitochondria, and the nucleus." Int Rev Cytol, 1996, 165:207-234 abstract.

Valentin-Weigand et al., "Correlation of epithelial cell invasiveness of group B *streptococci* with clinical source of isolation." Microb Pathog, 1995, 19 (2): 83-91 abstract.

Valentin-Weigand et al, "Characterization of group B *streptococcal* invasion in HEp-2 epithelial cells." FEMS Microbiol Lett, 1997, 147 (1): 69-74 abstract.

Verjans et al, "Entrance and survival of *Salmonella typhimurium* and *Yersinia enterocolitica* within human B—and T-cell lines." Infect Immun, 1994, 62 (6): 2229-2235 abstract.

Verma et al, "Construction of aromatic dependent *Shigella flexneri* 2a live vaccine candidate strains: deletion mutations in the aroA and aroD genes."Vaccine, 1991, 9 (1): 6-9 abstract.

Vicente et al, "Reacquisition of virulence of haemolysin-negative Listeria monocytogenes mutants by complementation with plasmid carrying the hlyA gene." Acta Microbiol Hung, 1989, 36 (2-3): 199-203 abstract.

Wachtel et al, "In vitro and in vivo characterization of an ail mutant of *Yersinia enterocolitica*." Infect Immun, 1995, 63 (7): 2541-2548 abstract.

Xiang et al, "Immune responses to nucleic acid vaccines to rabies virus." Virology, Jun. 1995, 209 (2): 569-579 abstract.

Yasutomi et al, "Simian immunodeficiency virus-specific cytotoxic T-lymphocyte induction through DNA vaccination of rhesus monkeys." J Virol, Jan 1996, 70 (1): 678-681 abstract.

Yokoyama et al, "DNA immunization: effects of vehicles and route of administration on the induction of protective antiviral immunity. "FEMS Immunol Med Microbiol, Jul. 1996, 14 (4): 221-230 abstract.

* cited by examiner

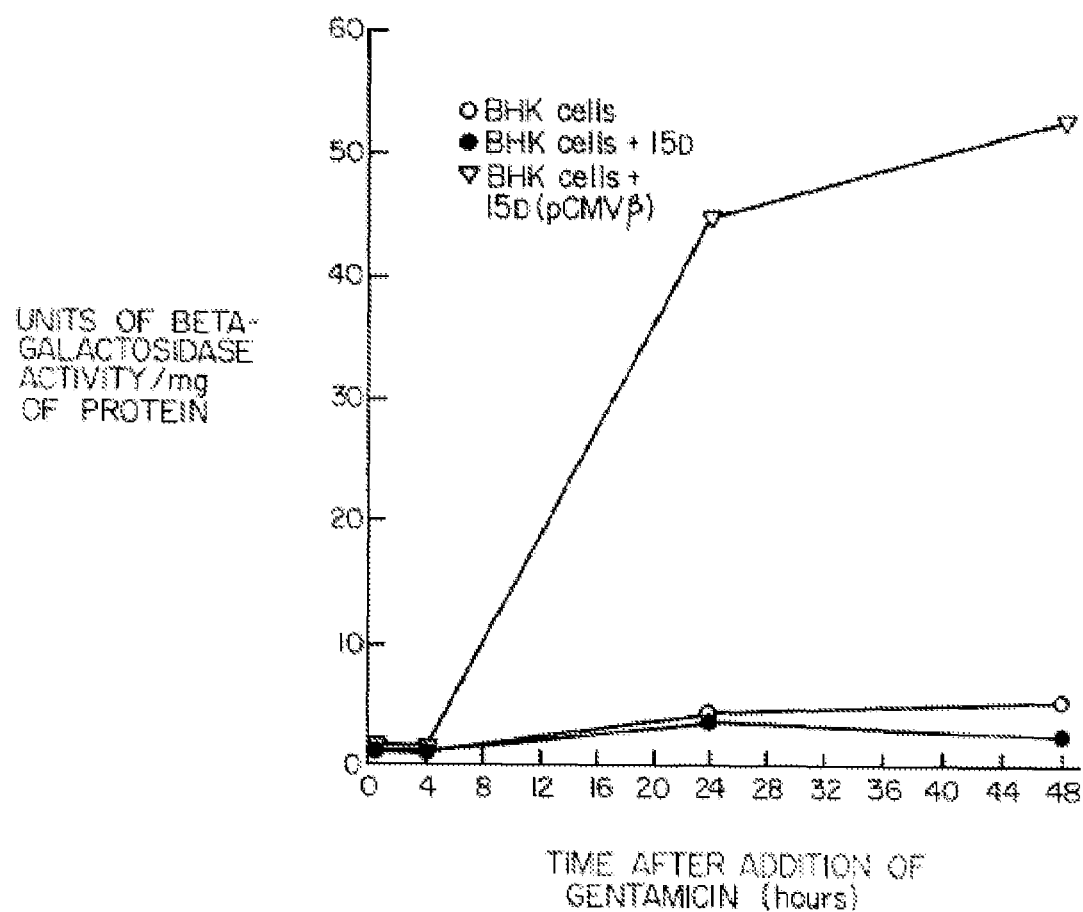

BACTERIAL DELIVERY SYSTEM

This application claims the benefit of U.S. Provisional Application No. 60/003,318 filed Sep. 6, 1995, and U.S. Provisional Application No. 60/018,035 filed May 21, 1999, and Ser. No. 08/523,855 filed Sep. 6, 1995, now U.S. Pat. No. 5,824,538 issued Oct. 20, 1998, Ser. No. 08/711,961 filed Sep. 6, 1996.

INTRODUCTION

This invention relates to a method for introducing functional nucleic acids into cells using a bacterial delivery system. A bacterial vector capable of delivering functional nucleic acids to cells can be produced by introducing a bacterial plasmid containing promoters and other instructions recognized by eukaryotic cells into bacteria capable of invading cells, or being taken up by cells, or capable of releasing the nucleic acids such that they are taken up by cells. The bacteria used in this delivery system do not have to be alive in order to deliver the nucleic acids of choice. The nucleic acids delivered to the cell in this way can direct the eukaryotic cell to produce antigens or other functional molecules.

These unique bacterial delivery systems therefor can be used as vaccines to prevent or treat infectious diseases and cancer, down regulate the immune system in the case of tissue rejection in transplantation, prevent or treat autoimmune diseases and other diseases related to dysregulation of the immune system. In addition, the bacterial delivery systems can be used for gene therapy or gene replacement for treatment or amelioration of disease such as hereditary genetic diseases, cancers and virus infections.

Direct DNA-mediated immunization is another approach to the introduction of functional nucleic acids and vaccine development. Highly purified bacterial plasmid DNAs expressing desired proteins under the control of viral promoters have been injected primarily into muscle or skin by traditional needle and syringe or by other more exotic methods such as biolistic transfection with DNA-coated gold microparticles (for review see Donnelly, J. J. et al. *J. Immunol. Methods* (1994) 176: 145). Investigators using this technology have been able to elicit neutralizing antibodies, cytotoxic T lymphocytes and protection to challenge in several animal models of infection ranging from influenza to malaria. The use of bacteria as a delivery system as described in this invention is a unique method of delivering DNA to mammalian cells and has the potential to provide a simple, inexpensive way of extending DNA immunization to the local immune system and beyond through oral and other mucosal routes of immunization.

Previously, live bacteria have been utilized as vaccines in order to protect against subsequent infection. Attenuated or less virulent *Shigella, Salmonella, Listeria,* and other bacteria have been given orally to immunize against subsequent infection with more virulent forms of these bacteria. Likewise, attenuated bacterial and mycobacterial organisms such as Bacille Calmette-Guerin (BCG) have been administered parenterally to protect against related organisms such as *M. tuberculosis.* Genes from bacteria, viruses and parasites have been cloned into a variety of bacteria and mycobacteria for the purpose of directing the bacteria to express the foreign antigen or impart on the bacteria certain desired properties for use as a live vaccine. Examples include cloning the invasion genes of *Shigella* into the normally non-invasive *E. coli* rendering the *E. coli* invasive and therefore more suitable for use as a vaccine strain, or cloning of *P. falciparum* malaria genes into *Salmonella typhimurium* which subsequently express these malaria proteins and, following oral administration of the bacteria, induce specific cytotoxic T cell immunity and protection in mice against malaria challenge (Sadoff et al. *Science* (1988) 240:336-338; Aggrawal et al. *J. Exp. Med.* (1990) 172: 1083-1090). All of these bacterial delivery systems require the bacteria itself to produce the antigen or functional molecule and are dependent on a bacteria which is sufficiently attenuated to be safe for use in humans, but still able to induce a protective response. The bacterial delivery system of the present invention is designed to deliver functional nucleic acids which direct eukaryotic cells to produce antigens and other functional molecules. In this case, toxicity to the carrier is eliminated becuase plasmid-encoded gene expression is dependent upon the machinery of the eukaryotic cell allowing proper folding of the antigen for presentation or direction of cell functions. In addition, if desired, it can be used to deliver prokaryotically produced antigens and functional molecules.

This invention can be applied to any desired bacteria. We chose *Shigella* as an example of a bacterial delivery system because of its ability to invade cells, escape from the phagosome, and enter into the cytoplasm of eukaryotic cells. These properties are not required of a bacteria chosen for application of the present invention, but simplified the experimental system. *Shigella* serves as an example of both nucleic acid delivery and bacterial antigen delivery with vaccine utility. *Shigellae* are enteric pathogens that invade the human colonic epithelium and multiply intracellularly, causing bacillary dysentery. Bacillary dysentery is caused by all members of the genus *Shigella* (*S. boydii, S. dysenteriae, S. flexneri,* and *S. sonnei*). Shigellosis is prevalent in developing countries, but is also found in industrialized nations, especially in institutional settings. It has been estimated that Shigellosis is the cause of half a million deaths a year, mostly among children, making the development of a safe and effective *Shigella* vaccine important (Stole, B. J. et al. *J. Infect. Dis.* (1982) 146: 177). All documents cited herein supra or infra are hereby incorporated by reference.

To cause dysentery, *Shigella* strains must be able to recognize, invade and multiply within epithelial cells of the colon (LaBrec, E. H. et al. *J. Bacteriol.* (1964) 88: 1503). Both the bacteria and host cell play a role in the invasive process wherein the host cell actively engulfs the bacteria which in turn escapes from the phagosome by a bacteria-mediated digestion of the phagosomal membrane (Sansonetti, P. J. et al. *Infect. Immun.* (1981) 34: 75). Once in the cell, bacterial multiplication occurs resulting in host cell necrosis.

Earlier studies have demonstrated that parenteral immunization with live or killed *Shigella* did not protect against infection (Formal, S. B. et al. *Proc. Soc. Exp. Bio. Med.* (1967) 25: 347; Higgins, A. R. et al. *Am. J. Trop. Med. Hyg.* (1955) 4: 281; Shaugnessy, H. J. et al. *JAMA* (1946) 132: 362). Recent efforts have focused on the development of an attenuated *Shigella* vaccine strain to induce mucosal immunity to *Shigella* antigens (Lindberg, A. A. et al. *Vaccine* (1988) 6: 146; Newland, J. W. et al. *Vaccine* (1992) 10: 766). Although several candidates have shown promise, no safe and effective vaccine has been found. Previously constructed *Shigella* vaccine candidates have either not elicited a protective immune response able to protect against subsequent challenge, or the strains were not sufficiently attenuated for use in humans.

Therefore, in view of the above, there is a need for a properly attenuated strain of *Shigella* which could serve as a vaccine candidate against *Shigella* infections as well as a bacterial vector for the delivery of heterologous and homologous antigens and for DNA-mediated immunizations, and gene delivery.

SUMMARY

In this invention is described an attenuated *Shigella* strain that can deliver functional nucleic acids to cells and deliver heterologous and homologous antigens. Even though a specific bacteria is described herein and is shown to deliver nucleic acids to eukaryotic cells whether the bacteria were alive or inactivated, this invention is applicable to all bacteria and mycobacteria. Plasmids introduced into other cells such as plant cells may also render these cells capable of delivering nucleic acids.

Specifically, the attenuated *Shigella* strain of the present invention is capable of delivering functional nucleic acids and serving as a vaccine candidate itself against *Shigella* infections. The attenuated *Shigella* strain of the present invention enters the cell but, once inside the host cell, dies releasing its contents. The attenuated *Shigella* strain described herein is sufficiently attenuated to not cause disease, while still maintaining the ability to enter mammalian cells. This strain is shown to be protective against *Shigella flexneri* 2a strain 2457T challenge in the guinea pig keratoconjunctivitis model, an animal model wherein the invasion of the corneal epithelium by *Shigella* mimics the process seen in the intestinal epithelium of the human or primate host (Mackel et al. *Am. J. Hyg.* (1961) 73: 219-223; Sereny, B. *Acta Microbiol. Acad. Sci. Hung.* (1962) 9: 55-60).

We chose to exploit the ability of *Shigellae* to enter epithelial cells and escape the phagocytic vacuole as a method to direct DNA to the cytoplasm of the host cell for protein synthesis and processing for antigen presentation (High, N. et al. *EMBO J.* (1992) 11: 1991). A mutation in the gene encoding aspartate β-semialdehyde dehydrogenase (ASD) was placed in *Shigella flexneri* 2a strain 2457T for the specific purpose of delivering DNA to mucosal epithelial cells of the gut. This resulted in a strain unable to grow in the absence of diaminopimelate (DAP), an essential peptidoglycan component comprising the cell wall of gram negative bacteria. DAP is not present in mammalian tissues, and is therefore unavailable for scavenge by infecting bacteria. This mutant strain of *Shigella* represents a highly attenuated bacterial vector, which is capable of invading mammalian cells and providing protective immunity against strain specific *Shigella* infection, as well as serving as a delivery vehicle for oral and other mucosal DNA immunization and gene therapy strategies.

Therefore, it is one object of the invention to provide an attenuated strain of *Shigella* which retains the ability to enter a cell, but dies once inside the cell. The attenuated strain of *Shigella* can be used as a vaccine for treatment or reduction of the severity or symptoms of disease caused by *Shigella* or for protection against *Shigella* infections.

It is another object of the invention to provide an attenuated and inactivated strain of *Shigella* which retains the ability to enter a cell, but dies once inside the cell. The attenuated and inactivated strain of *Shigella* can be used as a vaccine for treatment or reduction of the severity or symptoms of disease caused by *Shigella* or for protection against *Shigella* infections.

It is still another object of the invention to provide a method for attenuating different strains of *Shigella* for use as a protective vaccine against infection or for ameliorating disease symptoms caused by *Shigella* infection.

It is yet another object of the present invention to provide a vaccine for reducing in an individual disease symptoms caused by *Shigella* comprised of attenuated *Shigella* which retains the ability to enter the cell, but dies once inside the cell, and a pharmaceutically acceptable excipient.

It is further an object of the present invention to provide a delivery vehicle for the delivery of DNA to mucosal surfaces. The DNA encoding desired gene(s) or antigen(s) can be introduced into the described attenuated *Shigella* strain of the present invention or an attenuated/inactivated *Shigella* strain and the recombinant attenuated *Shigella* strain allowed to enter mammalian cells. Due to the mutation introduced into the attenuated strain, the recombinant attenuated *Shigella* will die once inside the cell, successfully delivering functional foreign DNA to mammalian cells. Such a delivery vehicle could be used for oral and other mucosal immunization and gene therapy strategies.

It is still another object of the present invention to deliver heterologous foreign antigens expressed by the attenuated *Shigella* for the purpose of inducing in an individual an immune response against the foreign antigen or for treatment of a disease wherein said foreign antigen is missing or found in reduced amount.

It is further another object of the invention to provide a delivery vehicle for delivery of DNA and antigens to cells in vitro for use of those cells in transplantation and gene therapy.

It is yet another object of the invention to provide an attenuated and an attenuated/inactivated strain of *S. flexneri* for use as a vaccine against *S. flexneri* infections.

Still another object of the invention is to provide an attenuated strain of *S. flexneri* which is mutant in the asd gene for use as a vaccine against infection by *S. flexneri*, for reducing the symptoms in an individual caused by such an infection, or as a delivery vehicle for heterologous antigens or DNA.

It is still another object of the invention to provide a method for introducing the invasion genes of *Shigella* into other bacterial species for the purpose of using new species of bacteria as DNA delivery vehicles.

A further object of the present invention is to provide a safer strain which can be used in diagnostic assays for detecting of disease caused by *Shigella* or determining exposure to *Shigella* in an individual and a kit therefor.

It is yet another object of the invention to provide *Shigella* components for the production of antibodies for use in a diagnostic assay for the detection of *Shigella* in a sample.

It is yet another object of the invention to provide a general method for introducing functional nucleic acids into cells using bacterial delivery systems for the purposes of induction of protective immunity as a vaccine, for the prevention and therapy of tumors, for the treatment and prevention of autoimmune disorders, for the treatment of conditions related to dysfunction of the immune system, for transplantation, for gene replacement, and gene therapy.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1:
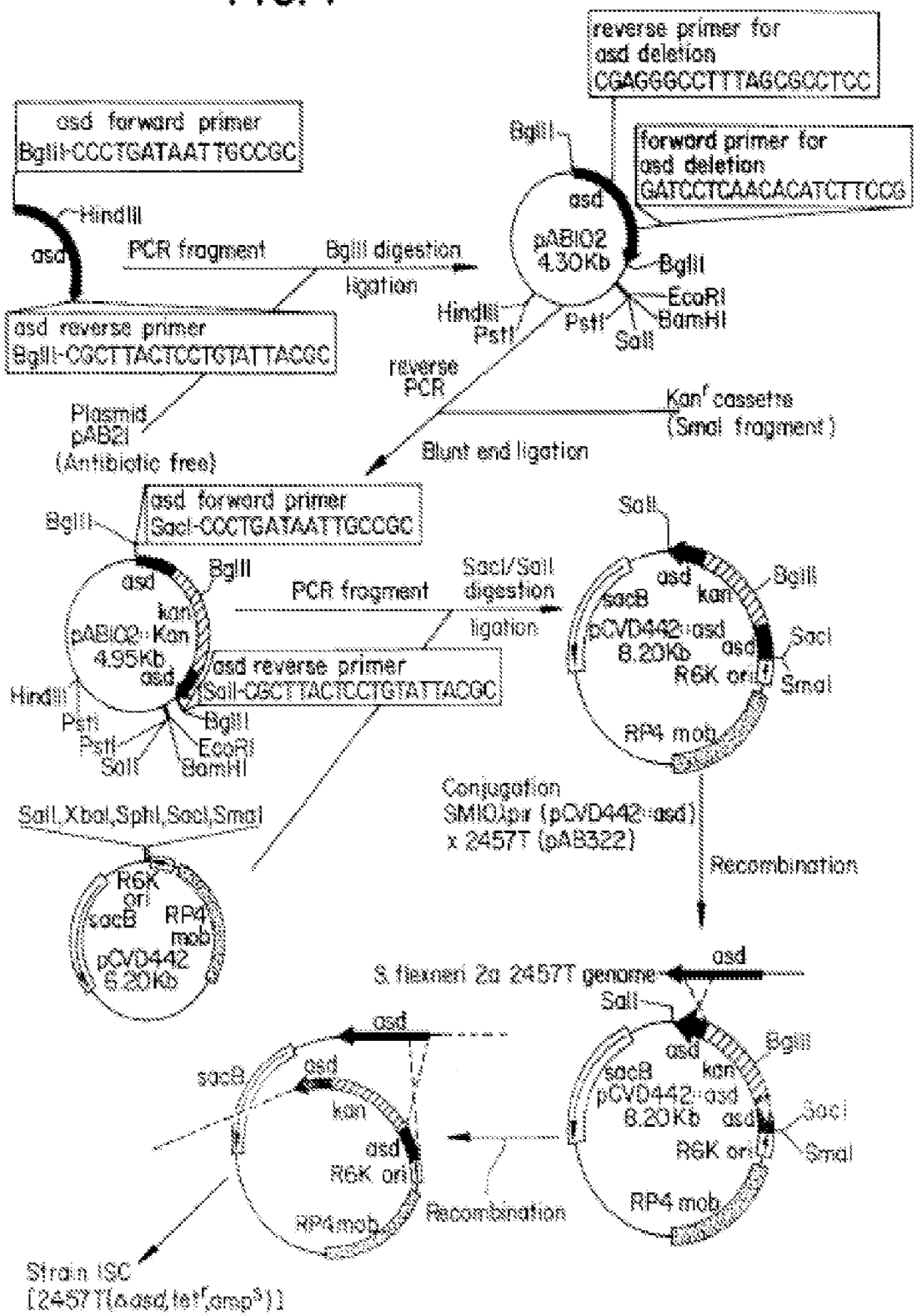
FIG. 1 shows the construction of a Δasd derivative of *Shigella flexneri* 2a strain 2457T1. The primers used are: BgIII-CCCTGATAATTGCCGC (SEQ ID NO:3), BgIII- CGCTTACTCCTGTATTACGC (SEQ ID NO:4), CGAGGGCCTTTAGCGCCTCC (SEQ ID NO:5), GATC-CTCAACACATCTTCCG (SEQ ID NO:6), SacI-CCCT GATAATTGCCGC (SEQ ID NO:7), and SaII-CGCT-TACTCCTGTATTACGC (SEQ ID NO:8)

The present invention describes an attenuated Shigella strain and a process for the production of an attenuated Shigella strain for use an an immunogen for protection against Shigella infections, and for use as a carrier for the delivery of heterologous antigens, for the delivery of DNA to mucosal surfaces, or for use in a diagnostic assay. This process is generally applicable to all bacteria and mycobacteria.

Specifically, the present invention describes the construction of an isolate of Shigella flexneri containing a deletion in the gene encoding aspartate β-semialdehyde dehydrogenase (ASD), an essential enzyme required for synthesizing the bacterial cell wall constituent diaminopimelic acid (DAP). Without being bound to a theory, this mutant strain retains the ability to enter mammalian cells, but once inside the cell, is not able to replicate due to the absence of DAP which is unavailable for scavenge from mammalian cells and as a result, the bacteria dies, releasing its contents including intact DNA and antigens already present in the bacteria.

More specifically, the Shigella flexneri 2a strain 2457T was mutated by integration of a deleted E. coli asd gene containing a 553 bp deletion from position 439 to 991 of the structural gene (SEQ ID NO: 1) into its chromosome. A kanamycin resistance cassette containing the complete Tn5 kanamycin gene was cloned between the flanking sequences of the mutant asd gene.

In accordance with the present invention, any Shigella strain can be mutated to provide an asd mutant as an attenuated strain. The strain does not need to be virulent, but preferably should have the ability to enter or be taken up by the target cell. The asd mutation will facilitate the destruction of the bacteria once the bacteria is inside the cell. In addition, any gene other than asd can be mutated to have the same effect on the bacteria, namely retain the ability to enter the cell and die once inside the cell or be attenuated to such an extent that clinical symptoms be acceptable. Examples of such genes include, but are not limtied to, thy A, genes for LPS production, htrA and htrB, and dut.

One method for creating a mutation in the asd gene is described in the examples below. Alternatively, a mutation in the gene of choice can be any chemical change in the DNA leading to a change in the genetic character such that the function of the gene product is lost or altered resulting in the inability of the bacteria to survive inside the host cell. Chemical changes in DNA include, but are not limited to, single or multiple deletion, single or multiple point mutation, integration of another gene or genes or portions of genes into the structural portion of the gene to be mutated, and the addition or deletion of transposons (Please see review by Kleckner et al. *J. Mol. Biol.* (1977) 116: 125). Strains which include mutations in addition to the asd mutation are contemplated, and are within the scope of the invention. The different mutations and methods for introducing these mutations are well known by a person with ordinary skill in the art (See Davis, R. W. et al. *Advanced Bacterial Genetics. A Manual for Genetic Engineering.* Cold Spring Harbor Laboratory, Cold Spring Harbor, N.Y., 1980).

Specifically, the attenuated *Shigella* 15D strain was prepared as follows. A gene encoding *E. coli* asd was amplified using PCR in order to incorporate restriction sites necessary for cloning into a vector. In accordance with the present invention, any homologous asd gene could be used to generate an asd deletion in *Shigella.* Homologous genes include, but are not limited to, asd sequences obtained from *Corynebacterium glutamicum, Bacillus subtilis, Mycobacterium smegmatis, Pseudomonas aeruginosa, Leptospira interrogans, Bordetella pertussis, Corynebacterium flavum, Neisseria meningitidis, Vibrio cholera, Mycobacterium bovis, Streptomyces skiyoshiensis, Streptococcus mutans, Vibrio mimicus,* and *Brucella* species. Any method of incorporating the necessary restriction sites for cloning into a vector of choice can be used such as the use of linkers or adaptors, blunt end cloning into a polylinker and other DNA cloning techniques known to a person of ordinary skill in the art (For review, please see *Current Protocols in Molecular Biology,* F. M. Ausubel et al. Eds. Greene Publishing Associates and Wiley-Interscience, New York). In addition, any vector which can be linearized for the insertion of the fragment of interest can be used for cloning and are known to people in the art. Examples of vectors include, but are not limited to, high copy plasmids, phagmids, single copy vectors, expression vectors, and phages.

The resulting plasmid with *E. coli* asd was reverse PCR amplified to delete 553 bp of the *E. coli* asd structural gene (position 439 to 991) to produce a mutant *E. coli* asd or Δ asd (SEQ. ID.NO:2). Any other method known to people in the art for introducing mutations, deleting genes or portions of genes can be used, such as, for example Bal 31 digestion, multiple restriction digestion or recombination.

After producing Δ asd, the kanamycin resistance (Kan$^r$) cassette from the commercial plasmid pUC4K-KIXX (Pharmacia) was purified and cloned between the flanking Δ asd sequences producing Δ asd::Kan$^r$. In accordance with the present invention, any gene or genes, whether for antibiotic resistance, or for the purpose of gene therapy or antigen production, can be inserted in the asd deletion. Methods for the formation of proper ends for fragment ligation are known to people in the art. Furthermore, it is not necessary to insert a gene in the asd deletion, the deletion itself is sufficient to confer the mutant phenotype and produce an attenuated *Shigella*.

Using forward and reverse primers containing restriction sites necessary for the insertion of the Δ asd::Kan$^r$ into the positive selection suicide vector pCVD442, PCR amplification resulted in a PCR fragment containing the asd gene with an internal deletion and the Kan$^r$ cassette with the proper restriction sites. Again, any method for the insertion of proper restriction sites, or for the preparation of fragment ends to be ligated such that ligation occurs can be utilized. Such methods are familiar to people in the art and are reviewed in Maniatis et al. *Molecular Cloning: A Laboratory Manual.* Cold Spring Harbor Laboratories, 1982. The vector pCVD442 is a mobilizable suicide vector containing sacB as a positive counter selection system for recombination. Any vector with an origin of replication that does not function in *Shigella* would serve as an acceptable suicide vector. In addition, a counter selective gene such as sacB, EF-G, klaA, B or C, λP gene, or the T7 bacteriaphage genes 1.2 or 10 is preferable but not necessary, for selection of transformants.

*E. coli* strain SM10λpir was used for transformations using the ligations of Δ asd::Kan$^r$ into the pCVD442. Any strain which allows for the propagation of the suicide vector, and is a suitable strain for conjugations in *Shigella* can be used. Vectors and suitable bacteria are within the knowledge of people in the art. The SM10λpir (pCVDZ422::Δ asd:: Kan$^r$) was conjugated to *S. flexneri* 2a strain 2457T (pAB322[Tet$^r$, Amp$^s$]) and Amp$^r$/Tet$^r$ conjugants selected. Conjugation of *Shigella* is well known to a person with ordinary skill in the art. Any method of tagging the recipient strain could be used. An auxotrophic marker or antibiotic marker allows for selection over the donor strain. Similarly, the suicide vector could be introduced directly into *Shigella* by transformation or electroporation. Growing the conjugants on sucrose, a standard protocol for sacB containing plasmids, resulted in a second recombination event producing the isolate 15D. This isolate has been deposited at the American Type Culture Collection, 10801 University Boulevard, Manassas, Va. 20110-2209, and given ATCC accession number ATCC 55710.

The isolate of choice was obtained by screening for Kan$^r$ and a requirement for DAP. The isolate of choice can be screened for a requirement for DAP if the mutation is in the ASD gene, or for a requirement for the product of the gene which was deleted, or for the presence of a gene inserted into the bacteria. Other screening methods are known to people in the art and dependent on the particular specifics of the strain. For example, positive selection could also be performed by scoring for a marker gene such as xylE which would be maintained between the recombining fragments.

In one embodiment, the present invention relates to a method for the delivery of a desired gene or genes into a cell, the method comprising the steps of:
(i) introducing the gene of interest into a strain of attenuated *Shigella;*
(ii) administering said *Shigella*.

In accordance with the present invention, any gene or genes can be introduced into the *Shigella* chromosome or virulence plasmid by methods described above, or alternatively can be carried by *Shigella* in a replicating or nonreplicating plasmid. The vectors of interest can be introduced via transformation, electroporation, transfection or conjugation. Genes for immunizations would include genes encoding foreign antigens from organisms causing, for example, diarrheal diseases such as rotavirus, sexually transmitted diseases such as human immunodeficiency virus, *Neisseria gonorrhoeae,* and human papilloma virus, and gastrointestinal diseases such as the ulcer causing *Helicobacter pylori.* The attenuated *Shigella* was shown to deliver DNA and antigens to cells whether the bacteria was alive or inactivated. Inactivation of bacteria is known in the art and can be achieved, for example, by heating to 56° C. for 30 minutes. Inactivation can only be performed to the extent that delivery of functional nucleic acids is not unduly compromised.

Delivery of DNA encoded antigens to the mucosal immune system by *Shigella* may permit mucosal immunization simultaneously with multiple antigens that can be directed for class I and/or class II presentation, stimulation of Th1 or Th2 help, or secreted while maintaining the proper folding and conformational epitopes for IgA and IgG antibody production.

Similar methods can be used for the delivery of DNA for gene therapy and correction of inborn errors of metabolisms. Such genes would include, for example, replacement of defective genes such as the CFTR gene for cystic fibrosis or introduction of new genes such as reverse transcriptase or protease antisense genes for the treatment of HIV or genes to upregulate Th1 immune responses such as interleukin-12 (IL-12) or genes to up- or down-regulate certain receptors, metabolites or hormones such as cholesterol and cholesterol receptors, insulin and insulin receptors, or genes encoding products that can kill cancer cells such as Tumor Necrosis Factor (TNF), or genes to upregulate systems that have decreased for a variety of reasons including aging such as secretion of growth hormone, stimulation of osteocytes to promote bone growth and down regulation of osteoclasts to decrease bone desorption.

Similar methods can be used for delivery of nucleic acids to down regulate the immune system in an antigen specific manner or general manner in order to prevent or control autoimmune diseases or other diseases involved in dysregulation of the immune system or for prevention or treatment of specific diseases or conditions including transplantation. Examples include the prevention or treatment of autoimmune encephalitis, multiple sclerosis, lupus erythematosis, diabetes melitus, Crohn's disease and other inflammatory bowel diseases, and rheumatoid arthritis and other inflammatory joint and skin diseases. Other examples include down regulation of immune responses that inhibit appropriate protective or curative immune responses such as down regulation of immune responses that distract from protective and curative immune responses to cancer and other diseases. For example, down regulation of Th2 responses when Th1 responses are appropriate for prevention and treatment of cancer, Leishmania, Mycobacterium tuberculosis, and HIV. This can be accomplished using this methodology through manipulation of the unique immunosuppressive properties of the gut and other local immune systems in combination with the ability to code for production of the appropriate cytokine milieu for induction of the appropriate immune response and suppression of inappropriate responses.

In another embodiment, the present invention relates to a method for the introduction of antigens of interest into cells. Such a method would comprise introduction of the desired DNA or antigen into attenuated or attenuated/inactivated Shigella such that the desired antigens are produced, and administering said Shigella to an individual. Said antigens can be produced during the life cycle of the Shigella prior to entering said cells. These antigens can be expressed from a prokaryotic promoter, and can either be constitutively expressed or induced. Such genes include those from parasitic organisms from which an immune response is desired.

In another embodiment, the present invention relates to a method for the introduction of DNA or antigens of interest into cells in vitro. Such a method would comprise introduction of the desired DNA or antigen into attenuated or attenuated/inactivated Shigella such that the desired antigens are produced, and administering said Shigella to cells. Shigella infects several different cells types, such as BHK (baby hamster kidney cells), HeLa (Human cervical epitheloid carcinoma), CaCo-2 (human colonic adenocarcinoma) and therefor is capable of delivering desired DNA or antigens into cells wherein said DNA can be expressed. Cells following DNA delivery can be transplanted for therapeutic purposes, for gene therapy or used as reagents in diagnostic assays.

In yet another embodiment, the present invention relates to a method for the production of invasive bacterial strains. The invasion genes that shigellae utilize can be inserted into other bacteria, such as E. coli, for example. Such a strain, now invasive, can be used as a carrier for the delivery of DNA to colonic mucosa. One advantage to using a delivery vehicle such as E. coli, a bacteria found in the natural flora of the intestine, is that the body will not raise an immune response against the bacteria, allowing multiple doses of the desired antigen or DNA to be introduced, and the immune response to be raised against the desired antigen and not against the bacteria delivering the foreign antigen. The virG gene, or other chromosomally encoded factors, and the virulence plasmid containing the virulence genes found in Shigella may be used to engineer an invasive strain from a non-invasive candidate (Please see Sansonetti et al. Infect. Immun. (1983) 39:1392).

In still another embodiment, the present invention relates to a vaccine against Shigella infection. The attenuated S. flexneri strain of the present invention can be used as an immunizing agent against S. flexneri infection. This strain has been shown to elicit a protective immune response in a guinea pig keratoconjunctivitis animal model. Other Shigellae strains can be attenuated similarly to the S. flexneri by introducing a mutation in a Shigellae gene as described above such that the resultant Shigella enters the cell and subsequently dies. Such a mutation can be in the asd gene for example, and the resulting attenuated strains used as a vaccine against infection with the specific serotype of shigellae strain used, for example S. boydii, S. dysenteriae, S. flexneri, and S. sonnei. The attenuated Shigella vaccine can be prepared in the form of a mixed vaccine which contains one strain or several different strains of attenuated Shigella. Further, the vaccine can include at least one other antigen as long as the added antigen does not interfere with the effectiveness of the attenuated Shigella vaccine and the side effects and adverse reactions, if any, are not increased additively or synergistically.

Vaccines are prepared for oral administration, either as liquid solutions or suspensions; solid form suitable for solution in, or suspension in, liquid prior to administration. The preparation may also be emulsified, or the ingredients are often mixed with excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations, nose drops or powders and contain about $10\text{-}10^{12}$ attenuated and/or attenuated/inactivated Shigella.

Vaccines can also be in the form of injectables. Suitable excipients would include, for example, saline or buffered saline (pH about 7 to about 8), or other physiologic, isotonic solutions which may also contain dextrose, glycerol or the like and combinations thereof. However, agents which disrupt or dissolve lipid membranes such as strong detergents, alcohols, and other organic solvents should be avoided. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and TIBI, which contains three components extracted from bacteria, monophosphoryl lipid A, trehalose dimycolate and cell wall skeleton (MPL+TDM+CWS) in a 2% sqalene/Tween 80 emulsion. The effectiveness of an adjuvant may be determined by measuring the level of desired immune response directed against the Shigella, carried antigen, or DNA encoded antigen resulting from administration of the attenuated Shigella, in vaccines which are also comprised of the various adjuvants.

The vaccine can be administered in the form of a liquid or suspension prepared as discussed above. Additional formulations which are suitable for other modes of administration include suppositories. Additionally, the vaccine can be lyophilized. For suppositories, traditional binders and carriers may include, for example, polyalkylene glycols or triglycerides; such suppositories may be formed from mixtures containing the attenuated Shigella enough to generate the desired immune response, i.e., protection or reduction of disease incidence or severity without causing undesirable, adverse side affects, generally in a range of $10\text{-}10^{12}$ colony forming units of attenuated Shigella per dose.

Generally, the vaccine may be administered orally, subcutaneously, intradermally, or intramuscularly in a dose effective for the production of the desired immune response. The vaccines are administered in a manner compatible with the dosage formulation, and in such amount as will be prophylactically and/or therapeutically effective. The quantity to be administered, which is generally in the range of or 10 to $10^{12}$ colony forming units of attenuated and/or attenuated/inactivated *Shigella* per dose, depends on whether it is acting as a vaccine to *Shigella* or a carrier of heterologous antigens or DNA, on the subject to be treated, capacity of the subject's immune system to develop the desired immune response, and the degree of protection desired. Precise amounts of the vaccine to be administered may depend on the judgement of the practitioner and may be peculiar to each subject, antigen, or use of the *Shigella* as a vaccine or carrier.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner. Examples of suitable immunization schedules include: (i) 0, 1 month and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms or reduce severity of disease. The generation of protective immunity against *Shigella* with an attenuated *Shigella* vaccine may reasonably be expected after a primary course of immunization consisting of 1 to 3 inoculations. These could be supplemented by boosters at intervals (e.g., every two years) designed to maintain a satisfactory level of protective immunity.

In a further embodiment, the present invention relates to a method of detecting the presence of *Shigella* antigens or an immune response against *Shigella*, in particular, *S. flexneri*, in a sample. One advantage of using the attenuated *Shigella* of the present invention is the reduction in cumbersome safety procedures necessary with highly infective natural *Shigella*; the attenuated *Shigella* presents a reduced risk to the operator due to the inability of the bacteria to survive inside the host cell.

Detection protocols may be based, for example upon competition, or direct reaction, or sandwich type assays. Protocols may also, for example use solid supports, or may be by immunoprecipitation. Most assays involve the use of a label; the labels may be, for example, fluorescent, chemiluminescent, radioactive, or dye molecules. Assays which amplify the signals from the probe are also known examples of which are assays which utilize biotin and avidin, and enzyme-labeled and mediated immunoassays, such as ELISA or ELISPOT assays. Using standard methodology well known in the art, a diagnostic assay can be constructed, for example, by coating a surface (i.e. a solid support) for example, a microtitration plate or a membrane (e.g. nitrocellulose membrane), with said attenuated *Shigella* described above or purified bacterial components from attenuated *Shigella*, for example, LPS and membrane or cellular components, and contacting it with the serum of a person suspected of having a *Shigella* infection. The presence of a resulting complex formed between the attenuated *Shigella* and antibodies specific therefor in the serum can be detected by any of the known methods common in the art, such as fluorescent antibody spectroscopy or colorimetry. This method of detection can be used, for example, for the diagnosis of *Shigella* infection, detection of immune responses, and determination of previous exposures to specific *Shigella* components.

In addition, bacterial components for example, LPS and membrane or cellular components, can safely be purified from attenuated *Shigella*, and may be used for the production of antibodies, monoclonal or polyclonal, for the detection of *Shigella* in a sample. The antibodies may be used to identify *Shigella* in the tissues or body fluids of individuals infected with *Shigella*, thus permitting rapid and accurate immunological diagnosis of such infections. The antibodies are also useful for the immunological detection of *Shigella* present as contaminants in water, biologicals, pharmaceuticals, or food. Detection is rapid, sensitive, and highly specific. A diagnostic composition can contain a concentration of the antibody effective to detect *Shigella*. The antibody can be packaged and sold in freeze-dried or other acceptable form for diagnostic use. It may be mixed with a suitable carrier, attached to an appropriate solid phase (e.g., latex particle, or plastic microtiter plate), conjugated with an enzyme or dye, or radiolabeled, depending on what immunological method is employed. If the antibody is found to neutralize *Shigella*, or reduce infection, it can be used for immunoprophylaxis or therapy of *Shigella* infections, or their consequences.

In still another embodiment, the present invention relates to a diagnostic kit which contains the attenuated *Shigella* and ancillary reagents that are well known in the art and that are suitable for use in detecting the presence of *Shigella* as contaminants in food, water, biologicals and pharmaceuticals, or for the detection of immune responses to *Shigella* in samples. Samples for detection of immune responses to *Shigella* would be serum and tissue samples from human, monkeys, or other mammal. The appropriate reagents and materials required for the conduct of the assay can be packaged along with a suitable set of assay instructions.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLE 1

Construction of an Attenuated *S. flexneri* 2a Strain

In constructing an appropriate strain, we chose to take advantage of the already popular conditional-lethal mutation system. A deletion mutation was made in the gene encoding ASD, an essential enzyme required for synthesizing the bacterial cell wall constituent diaminopimelic acid (DAP) (Nakayama et al. *BioTechnology* (1988) 6: 693). FIG. 1 illustrates the construction of 15D, a Δasd isolate of *Shigella flexneri* 2a strain 2457T. The gene encoding for *E. coli* asd (Haziza et al. *EMBO J.* (1982) 1: 379) was amplified using PCR, incorporating BglII restriction sites. asd was cloned into a previously described vector (Branstrom et al. Presented at the 33rd ICAAC, New Orleans, La., 20 Oct. 1993, Abstract #1136) and selected from using *E. coli* $_\chi 6097$ (Nakayama et al., supra). The resulting pAB102 plasmid was reverse PCR amplified to delete 553 bp of the *E. coli* asd structural gene (position 439 to 991) [all primers given in a 5' to 3' orientation, SEQ ID NO:3-8]. The kanamycin resistance cassette from the commercial plasmid pUC4K-KIXX (Pharmacia) was purified as a SmaI fragment and cloned between the flanking asd sequences. Using forward and reverse primers containing restriction sites SacI and SalI, respectively, PCR amplification resulted in a 2 kb PCR fragment containing the asd gene with an internal deletion and the Kan[r] cassette. The entire Δasd::Kan[r] PCR fragment was cloned into the SacI/SalI site of the positive selection suicide vector pCVD442 (Donnenberg and Kaper, *Infect. Immun.* (1991) 59: 4310). Ligations were transformed into SM10λpir (Simon et al. *BioTechnology* (1983) 1: 784) and selected by ampicillin resistance. SM10λpir (pCVD422::asd) was conjugated to *S. flexneri* 2a 2457T (pAB322[Tet[r], Amp[2]]) and Amp[r]/Tet[r] conjugants selected. PCR analysis determined that the isolates obtained that were integrated into the chromosome had recombined with the downstream portion of asd on the pCVD442 plasmid. Growing these isolates on sucrose resulted in a second recombination event (Quandt and Hynes, *Gene* (1993) 127: 15). Screening for Kan[r] and a requirement for DAP, isolate 15C was obtained. Hybridization and PCR analysis confirmed this strain as having a deletion in asd. This mutation could be complemented with *E. coli* asd cloned in a low copy number vector, restoring the original phenotype. 15C was cured of its Tet[r] plasmid by fusaric acid treatment (Maloy and Nunn, *J. Bacteriol.* (1981) 145: 1110) to generate isolate 15D.

EXAMPLE 2

Characterization of Isolate 15D

Strain 15D was able to maintain the commercially available eukaryotic expression vector pCMVβ without antibiotic selection. pCMVβ expresses *E. coli* β-galactosidase under the control of the immediate early promoter and enhancer from the human cytomegalovirus (CMV) in mammalian cells, which permitted us to easily analyze mammalian-mediated gene expression after delivery (MacGregor and Caskey, *Nucl. Acids Res.* (1989) 17: 2365).

Strain 15D was screened to ensure that the large plasmid essential for bacterial invasion of mammalian cells had not been lost during the genetic manipulations. Strain 15D was found to express the virulence associated polypeptides, IpaB and IpaC, as determined by immunoblotting (Mills et al. *Infect. Immun.* (1988) 56: 2933) showing no loss of the invasion plasmid. It was important to demonstrate that *Shigella* containing a mutation in a gene required for cell wall synthesis could still adhere to and invade cells in culture. Strains 15D and 15D(pCMVβ) were each tested for the ability to invade cultured baby hamster kidney (BHK) cells with and without supplementation of DAP during the 90 minutes allowed for invasion (Oaks et al. *Infect. Immun.* (1985) 48: 124). After this period of interaction, monolayers were extensively washed and treated with gentamicin (50 μg/ml) containing medium for at least 30 minutes to eliminate extracellular bacteria. Both constructs were found to invade BHK cells; however, the addition of DAP during bacterial-cell interaction significantly increased the number of 15D and 15D(pCMVβ) colonies recovered (Table 1). Fixed and stained chamber slides of infected BHK cell monolayers examined by light microscope verified viability findings. Without the presence of DAP during the invasion step, 15D and 15D(pCMVβ) entered just 13% and 10% of the BHK cells, respectively. By contrast, 33% (15D) and 29% [15D(pCMVβ)] of the BHK cells contained bacteria when DAP was included. Since the purpose of this study was to determine if bacteria could be used to deliver plasmid DNA to mammalian cells, DAP was added to concentrated bacteria during the adherence and invasion step in the following representative data.

TABLE 1

Growth of Δasd derivatives of *Shigella flexneri* 2a strain 2457T in cultured mammalian cells with and without the presence of DAP.

| | | Visual Observation: | |
|---|---|---|---|
| Strain: | Viable Bacteria: (mean +/− SD) | % of cells infected | Number of bacteria per cell (mean +/− SD) |
| 15 D | 1070 +/− 1071 | 13 | 1.95 +/− 1.22 |
| 15 D + DAP | $8.2 \times 10^4$ +/− $1.7 \times 10^4$ | 33 | 2.18 +/− 1.51 |
| 15 D(pCMVβ) | 1095 +/− 888 | 10 | 1.2 +/− 0.56 |
| 15 D(pCMVβ) + DAP | $8.62 \times 10^4$ +/− $6.07 \times 10^4$ | 28.6 | 1.76 +/− 1.21 |

Intracellular bacterial viability and β-galactosidase activity were followed over a 48 hour time course. For assaying viable bacteria recovered from infected BHK cells, the following protocol was followed. $1 \times 10^5$ BHK cells were plated in wells of a 24-well plate. This assay was adapted from those described previously for *Shigella* plaque analysis (Mills et al. *Infect. Immun.* (1988) 56: 2933; Oaks et al. *Infect. Immun.* (1985) 48:124). A single congo red-binding positive colony (denoting the expression of plasmid-encoded *Shigella* virulence determinants) of each strain was used to inoculate overnight LB broth cultures containing 50 ug/ml DAP [15D] or DAP plus 250 μg/ml of amplicillin [(15D(pCMVβ)]. Overnight cultures were diluted 1:50 and grown to approximately mid-log phase in the presence of DAP. Two hundred microliters of a 10X bacterial solution in HBSS with or without the addition of 50 ug/ml DAP were added to three wells of semi-confluent BHK cells, which had been washed with DMEM (BioWhittaker), at approximately 50:1. Bacteria were allowed to interact with the BHK cells in this minimal volume for 90 minutes at 37° C., 5% $CO_2$. Non-adherent bacteria were removed by extensive washes with HBSS. Extracellular bacteria were then killed by the addition of DMEM with 10% heat inactivated FBS (Bio-Whittaker) and 50 μg/ml gentamicin. At the indicated time points, cells were lysed with a 0.2% Triton-X-100 solution and appropriate dilutions plated on TSA congo red DAP plates for determination of viable bacterial counts.

For visual examination of fixed and stained chamber slides, 1X $10^5$ BHK cells were plated in Nunc chamber slides and infected with 15D and 15D(pCMVβ) as described above. At the appropriate times, chamber slides were extensively washed, fixed and stained with a Leukostain set (Fisher). At least 450 cells were visually examined by light microscopy for data analysis. An Instat statistical program (Graphpad, San Diego, Calif.) was used to calculate means and standard deviations.

EXAMPLE 3

Expression of DNA Delivered to Cells by Strain 15D

Figure 2A:
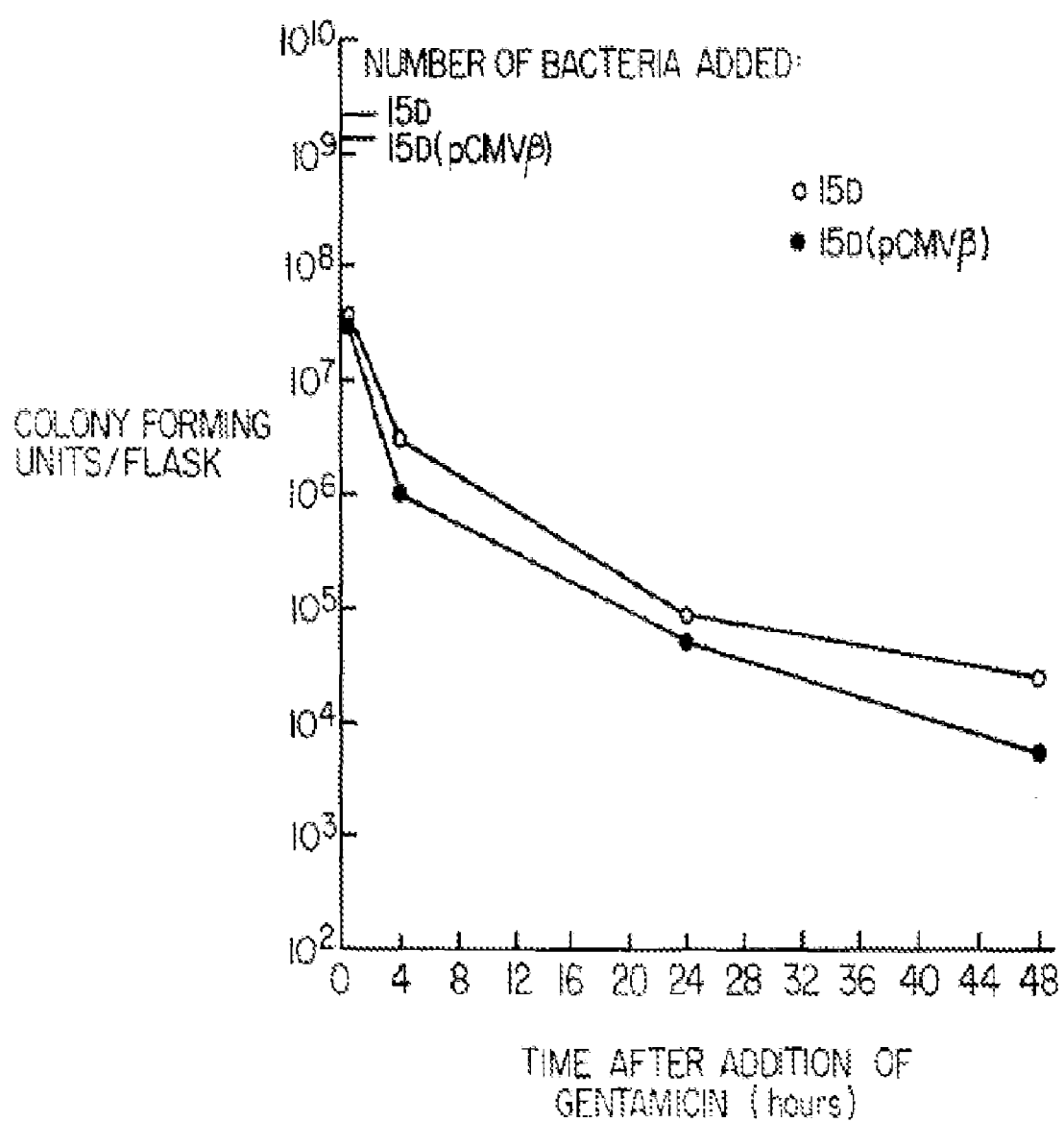
FIG. 2 represents results from the use of strain 15D as a carrier to deliver pCMVβ, a mammalian DNA expression plasmid, to BHK cells. (a) The number of surviving 15D (o) and 15D(pCMVβ)(•) were determined over a 48 hour time course. (b) Units of β-galactosidase activity per mg protein were also determined for BHK cells alone (o), BHK cells infected with 15D (•) and BHK cells infected with 15D (pCMVβ) (∇). A flask of semi-confluent BHK cells consists of approximately 0.5-1×10$^7$ cells. Determinations of β-galactosidase activity were made on an estimated 0.5×10$^7$ cells.

Bacteria were grown as described in Example 1 except that the bacterial suspensions were concentrated 10-fold and 2 mls were added to each flask. In this assay, 50 μg/ml of DAP was added to bacterial suspensions prior to their addition to flasks of semi-confluent BHK cells. Bacteria were added at a ratio of approximately 100:1. At the indicated time points, BHK cells were removed by trypsinization and washed in PBS. A portion of the cell suspension was lysed with a 0.2% Triton-X-100 solution and plated on TSA congo red DAP plates for determination of viable bacterial counts. The remainder of the cells were assayed for β-galactosidase activity. β-galactosidase activity was measured in the remaining cell extract by a standard biochemical assay that uses the conversion of o-nitrophenol-β-D-galactoside (ONPG) to galactose and the chromophore o-nitrophenol to quantitatively detect activity spectrophotometrically (Nolan et al. in *Methods in Molecular Biology*, E. J. Murray and J. M. Walker, Eds. (Humana Press Inc., Clifton, N.J., 1991) Vol. 7: 217-235). Units of β-galactosidase=380 X OD420/Time (minutes). Total protein concentrations of cellular extracts were determined via a BCA*protein assay kit (Pierce). Results are shown in FIGS. 2a and 2b.

Initially $1\text{-}3\times10^7$ viable bacteria of each strain were recovered from monolayers of BHK cells with no detectable β-galactosidase activity in cell extracts. Measurements of β-galactosidase activity in bacterial extracts equivalent to the total number of bacteria added were negative. After 4 hours, a 1 log to 1.5 logs loss in viable bacteria occurred with no detectable β-galactosidase activity. An additional log to 1.5 logs loss of viable bacteria was observed at both the 24 and 48 hour assay points. At both times, increasing units of β-galactosidase activity were readily detectable in cell extracts from BHK cells infected with 15D(pCMVβ). β-galactosidase activity detected at these last assay points was not due to expression from within the bacteria because no activity was detected at the first two assay points, yet a high level of viable bacteria were present. In addition, a noninvasive isolate of 15D(pCMVβ) (i.e., IpaB and IpaC immunoblot negative) was tested for the ability to deliver plasmid DNA. No β-galactosidase activity was detected at the 24 hour assay point.

This finding reinforces the hypothesis that to deliver DNA the bacteria must be capable of entering the mammalian cell and breaking out of the phagocytic vacuole, which most likely occurs during the first 4 hours of this assay. By the 24 and 48 hour assay points, sufficient time had passed for death of the bacterium and release of the plasmid DNA into the cell cytoplasm. This is followed by transcription and translation of the encoded reporter gene. Extracellular lysis of bacteria leading to the release of plasmid DNA with subsequent uptake by eukaryotic cells cannot account for these findings since the noninvasive isolate was unable to induce β-galactosidase activity.

EXAMPLE 4

Strain 15D as a DNA Delivery Vehicle

Figure 3:
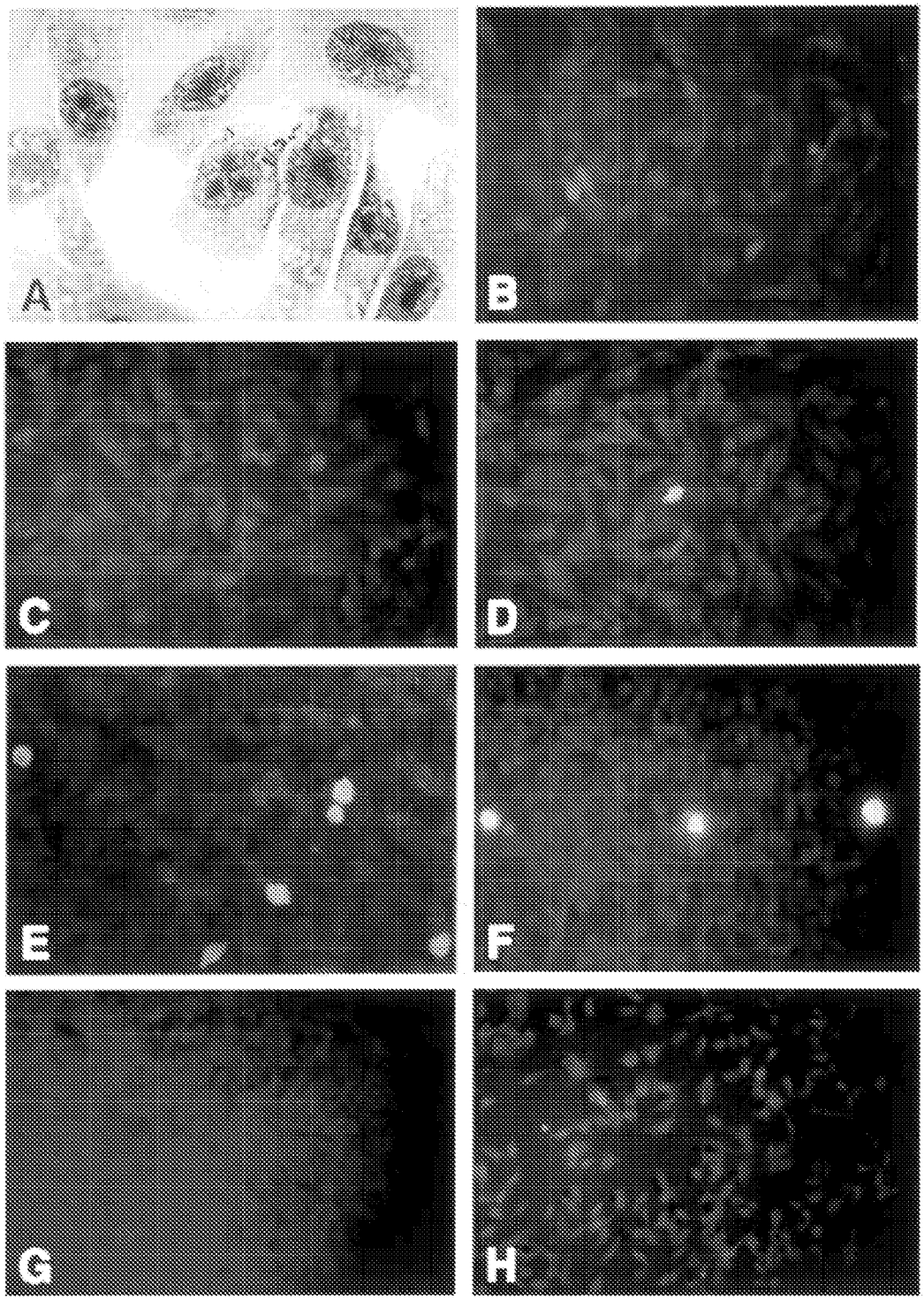
FIG. 3 shows results of intracellular immunostaining to detect expression of β-galactosidase in BHK cells infected with 15D and 15D(pCMVβ). (A) Leukostat stained BHK monolayer infected with 15D(pCMVβ) 30 minutes after the addition of gentamicin containing medium (100X oil immersion lens). Immunostained infected BHK cells after the addition of gentamicin containing medium: (B) 15D (pCMVβ) 30 minutes, (C) 15D 4 hours, (D) 15D(pCMVβ) 4 hours, (E) 15D(pCMVβ) 24 hours, (F) 15D(pCMVβ) 48 hours, (G) 15D 24 hours and (H) BHK cells alone; (B-H 10X fluorescence phase lens).

To verify the delivery of pCMVβ DNA to BHK cells, infected monolayers were immunostained to visually detect intracellular β-galactosidase expression within individual cells. As described in Example 1, 3 wells of a 4-well chamber slide of BHK cell monolayers infected with either 15D or 15D(pCMVβ) were immunostained to detect β-galactosidase expression (Sander et al. *J. immunol. Methods* (1993) 166:201). At each assay point, monolayers were fixed in phosphate-buffered 4% paraformaldehyde for 5 min. and subsequently blocked with 3% goat serum (Gibco-BRL) in HBSS for 30 min. BHK cells were then permeabilized for 1 min. with HBSS containing 0.1% saponin (Sigma) solution. Monoclonal anti-β-galactosidase (Sigma) was diluted 1:2000 in 0.1% saponin/HBSS and applied for 30 min. at 37° C. in a humidified chamber. Secondary anti-mouse IgG (Fc specific) FITC conjugated (Sigma) was diluted 1:32 and applied for 30 min. at room temperature. Between each step chamber slides were washed extensively with 0.1% saponin/HBSS solution. A final wash step of HBSS alone was used to close permeabilized cells. Fluorescent images were visualized with either a Nikon microphot with Epi-fluorescence attachment or an Olympus-VAN04-S with fluorescence attachment. Results are shown in FIG. 3.

No apparent intracellular immunostaining was observed in monolayers infected with either strain at the 30 minute assay point (FIG. 3A, B). Only slight intracellular immunostaining was detected at the 4 hour assay point in monolayers infected with 15D(pCMVβ) (FIG. 3C, D). At the 24 and 48 hour assay points, several cells per field of monolayers infected with 15D(pCMVβ) were positively stained (FIG. 3E, F). Staining throughout the cell cytoplasm indicated that the plasmid DNA had been released from the bacterium into the cell cytoplasm for further processing (i.e., transcription and translation) by the mammalian cell. Positively staining cells also appeared to be rounded, possibly due to the presence of an extensive amount of β-galactosidase protein. Approximately 1-2% of 5000 cells were stained positive for β-galactosidase expression at the 24 hour assay point as determined by fluorescence activated cell sorter (FACS) analysis (Nolan et al., supra). Visual examination of Leukostat stained chamber slides of 15D (pCMVβ) infected BHK cells demonstrated that 28% of the cells contained 1 to 5 intact bacterial cells with 1.7% containing 5 bacteria (Table 2). Four hours after gentamicin treatment 26% of the cells contained visually intact bacteria with less than 1% of the cells containing 4 bacteria. Therefore, invasion with between 1-5 bacteria was required for foreign gene expression. Since pCMVβ is a 7164 base pair plasmid of medium to high copy number with approximately 500 copies per bacterial cell, each bacterium is estimated to contain about 3.93 $(10^{-9})$ μg of DNA. Intracytoplasmic delivery of approximately $4\text{-}20\times10^{-9}$ μg of DNA by *Shigella* is sufficient for expression of β-galactosidase.

TABLE 2

Visual examination of infected BHK cells.

| Strain | Time | % Infected | Bacteria per BHK mean (SD) | Total number of BHK cells containing: Number of Bacteria: | | | | | | |
|---|---|---|---|---|---|---|---|---|---|---|
| | | | | 1 | 2 | 3 | 4 | 5 | 6 | Total: |
| 15 D | 30' | 39.3 | 1.84 (1.2) | 96 | 47 | 14 | 14 | 3 | 3 | 177 |
| | 4 hrs | 35.8 | 1.68 (0.94) | 106 | 36 | 13 | 5 | 0 | 1 | 161 |
| | 24 hrs | 3.7 | 1 | — | — | — | — | — | — | |
| | 48 hrs | 2.2 | 1 | — | — | — | — | — | — | |
| pCMVβ | 30' | 28 | 1.35 (0.72) | 76 | 29 | 7 | 5 | 2 | 0 | 119 |
| | 4 hrs | 25.95 | 1.4 (0.74) | 95 | 16 | 4 | 1 | 0 | 0 | 116 |
| | 24 hrs | 3.3 | 1 | — | — | — | — | — | — | |
| | 48 hrs | 3.8 | 1 | — | — | — | — | — | — | |

Percentage of BHK cells infected and number of bacteria per infected BHK cell. Chamber slides and bacteria were prepared as described in Table 1. Data are presented as the mean percentage of infected BHK cells and mean +/- standard deviation (SD) of bacteria per infected BHK cell.

EXAMPLE 5

Gene Delivery by *Shigella* to Different Cell Types

*Shigella* species invade many different types of cells. To demonstrate that gene delivery was not restricted to BHK cells, P815 cells were infected with 15D(pCMVβ). Bacteria used to infect P815 cells were grown as described in Example 1. After the addition of the bacteria with DAP to the non-adherent P815 cells cultured in 6-well plates, the plate was spun at 500×g for 5 minutes. Bacteria and P815 cells were allowed to interact for 90 minutes. The cells were then extensively washed with DMEM and resuspended in DMEM containing 100 μg/ml gentamicin for a one hour incubation at 37° C., 5% $CO_2$. The cells were again extensively washed and resuspended in DMEM containing 20 μg/ml gentamicin for overnight culture at 37° C., 5% $CO_2$ β-galactosidase activity and protein concentrations were determined at 24 hours as described (Nolan et al., supra).

As shown in Table 3, 10 fold higher levels of β-galactosidase were expressed compared to background control at 24 hours. P815 cells, which express $H-2^d$ class I MHC molecules, have been successfully infected with 15D (pCMVβ) and experiments are currently underway to determine if these cells can present Shigella delivered DNA encoded foreign antigens in the context of class I.

TABLE 3

β-galactosidase activity in P815 cells after infection with 15 D(pCMV β).

| Source: | Units of β-galactosidase/mg protein: |
|---|---|
| P815 cells | 3.04 |
| P815 cells + 15 D | 5.62 |
| P815 cells + 15 D(pCMVβ) | 56.25 |

EXAMPLE 6

15D Provides Protection Against Infection by Shigella in vivo

Experiments in a guinea pig keratoconjunctivitis challenge model demonstrate 100% protection from subsequent Shigella infection three weeks following a two dose immunization regime. Animals were immunized with $1-4\times10^8$ colony forming units per eye of days 0 and 15. Challenge occurred 3 weeks after final immunization. Animals were challenged with $3.8\times10^8$ virulent 2457T.

TABLE 4

Guinea Pig Challenge Summary

| EXP. | No. of eyes with rating of: | | | | | Protection: | | Combined % |
|---|---|---|---|---|---|---|---|---|
| | 0 | 1 | 2 | 3 | 4 | Full | Partial | |
| A | | | | | | | | |
| 1x dose 2 | 2 | 0 | 0 | 0 | | 50 | 50 | 100 |
| 5x dose 1 | 1 | 0 | 0 | 0 | | 50 | 50 | 100 |
| Control 0 | 0 | 0 | 0 | 4 | | | | |

After immunizations on days 0 and 14, animals were challenged 3 weeks later with $2.5 \times 10^8$ virulent 2457T.

| B | | | | | | | | |
|---|---|---|---|---|---|---|---|---|
| 1x dose 2 | 2 | 0 | 0 | 0 | | 50 | 50 | 100 |
| 5x dose 2 | 0 | 0 | 0 | 0 | | 100 | 0 | 100 |
| Control 0 | 0 | 0 | 0 | 10 | | | | |

After immunization on days 0 and 14, animals were challenged 3 weeks later with $5 \times 10^8$ virulent 2457T.

| C Strain: | | | | | | | | |
|---|---|---|---|---|---|---|---|---|
| 15 D | 2 | 6 | 0 | 0 | 0 | 25 | 75 | 100 |
| pCMV β 1 Heat-killed | 7 | 0 | 0 | 0 | | 13 | 87 | 100 |
| pCMV β 0 | 4 | 4 | 0 | 0 | | 0 | 50 | 50 |
| Controls 0 | 0 | 0 | 6 | 2 | | 0 | 0 | 0 |

*Animals above were immunized with between $2.5–3 \times 10^8$ colony forming units per eye with strain 15 D on days 0 and 14.
pCMV β: 15 D carrying a commercially available eukaryotic expression plasmid.
Heat-killed: heat to 56° C. for 30 minutes.

Eyes from animals in experiment C were also stained for β-galactosidase activity. Eyes from animals inoculated with 15D(pCMVβ) and 15D(pCMVβ) heat-killed showed staining. Less staining was detected in heat-killed 15D(pCMVβ) inoculated animals. These results demonstrate that this highly attenuated strain, which is capable of DNA delivery, functions well in vivo in the guinea pig keratoconjunctivitis model, and provides protection against challenge with Shigella, even when the bacteria is inactivated.

EXAMPLE 7

Guinea Pig Proliferation Assay

The purpose of this experiment was to determine the immune responsiveness of animals at the time of challenge as well as during the recovery period.

The spleens or cervical nodes of two animals were pooled for testing. Two challenged animals from each group were sacrificed 3 and 4 weeks post challenge for testing. Proliferative responses were tested on animals being analyzed for protection. Pre-challenge-animals were vaccinated as described and organs tested at the time other animals were being challenged.

Spleens and cervical nodes were processed to a single cell suspension and plated in 96 well plates at a concentration of $1-2\times10^5$ cells per well in 100 μl. Ten μl of each stimulus was added to the appropriate wells. After three days in culture, the amount of proliferation that had taken place was measured using a non-radioactive kit. Responses are presented in Table 5 below.

TABLE 5

| | Stimulation Index | | | | | |
|---|---|---|---|---|---|---|
| | Spleen | | | Cervical Nodes | | |
| | ConA | LPS | H.K. | ConA | LPS | H.K. |
| pre-challenge | | | | | | |
| 15 D | 3.9 | 1.6 | 1.85 | 0.42 | N.P. | 2.3 |
| 15 D(pCMV β) | 2.2 | 1.2 | 0.9 | 2.46 | 1.55 | 3.2 |
| Heat-killed | | | | | | |
| 15 D(pCMV β) | 1.15 | 0.7 | 0.675 | 1.15 | 3.55 | 2.8 |
| 3 weeks post challenge | | | | | | |
| 15 D | 0.78 | 4.25 | 2.4 | 2.36 | N.P. | 1.18 |
| 15 D(pCMV β) | 0.77 | 4.25 | 1.5 | 0.56 | N.P. | 0.59 |
| Heat-killed | | | | | | |
| 15 D(pCMV β) | 0.87 | N.P. | N.P. | 0.54 | 8.25 | 1.9 |
| 4 weeks post challenge | | | | | | |
| 15 D | 2.05 | N.P. | (0.039)* | 0.79 | N.P. | 0.23 |
| 15 D(pCMV β) | 1.8 | (.036)* | N.P. | 0.30 | 0.69 | 0.26 |
| Heat-killed | | | | | | |
| 15 D(pCMV β) | 0.89 | (.130)* | (.105)* | 0.68 | 0.31 | 0.38 |
| Challenged | 2.08 | (.180)* | (.091)* | 0.52 | 1.69 | 0.56 |
| Naive | | | | | | |

N.P.-no proliferation detected
*naive animal showed no detectable response: therefore, actual O.D. values are presented.
ConA-concanavalin A 5 μg/ml
LPS-commercial preparation from *E.coli* 250 pg/ml
H.K.-heat-killed *Shigella flexneri* 2a strain 2457T 5 μg/ml
All responses were averaged (i.e., 3–4 wells) and the average background response subtracted to determine the O.D. 490 values. Stimulation index was calculated by dividing the average experimental O.D. value by that of the naive control.

These results given insight into the immune responses (T cell and B cell involvement as measured by mitogenic responses, and specific responses to heat-killed antigen) to this highly attenuated strain at the time of challenge and during the weeks post challenge. Proliferation to β-galactosidase protein was not detected. Due to the normal immunological characteristics of the eye, this result was expected (Rocha and Baines *Critical Rev. Immun.* (1992) 12:81–100).

EXAMPLE 8

Mouse Intranasal Challenge Proliferation

The purpose of this experiment was to measure in an alternative model (i.e. murine intranasal) the ability of 15D to deliver DNA in vivo. In addition, immune responses to the carrier were also determined.

Groups of five mice each were inoculated twice intranasally 4 weeks apart. For each strain or treatment, three different doses were also given. Amounts are indicated below. One treatment group consisted of mice given 15D (pCMVβ) with 50 μg/ml of DAP added to the culture prior to inoculation. Four weeks after the second inoculation, spleens were removed, processed to a single cell suspension and plated in 96 well plates at 2×10⁵ cells per well in 100 μl. The μl of the stimuli were added to the appropriate wells. Plates were incubated for three days, and the amount of proliferation that had taken place was measured using a non-radioactive kit. Values were averaged and the background subtracted to determine the O.D. 490 value. Stimulation index for ConA, *E. coli* LPS and heat killed 2457T was calculated by dividing the average experimental O.D. value by that of the naive control. Results are shown in Table 6 below. Stimulation Index for β-gal is experimental (pCMVβ) O.D. value divided by that of 15D.

TABLE 6

| | Stimulation Index | | | | |
|---|---|---|---|---|---|
| | Stimulation Index = Exp/Control | | | Stimulation Index = pCMVβ/15 D | |
| | ConA 5 μg/ml | *E.coli* LPS 250 pg/ml | Heat-killed 2457T 5 μg/ml | β-gal protein$^A$ 0.25 μg/ml | β-gal protein$^A$ 2.5 μg/ml |
| 15 D(high) | 1.16 | 0.71 | 0.93 | — | — |
| (middle) | 1.34 | 0.68 | 0.73 | — | — |
| (low) | 1.10 | 0.52 | 0.84 | — | — |
| 15 D(pCMV β) (high) | 1.22 | 0.57 | 1.34 | 2.37 | 2.09 |
| (middle) | 1.12 | 0.77 | 1.49 | 2.09 | 2.39 |
| (low) | 1.15 | 0.61 | 1.17 | 0.66 | 0.7 |
| 15 D(pCMV β + DAP (high) | 0.85 | 1.29 | 1.27 | 3.12 | 3.6 |
| (middle) | 1.16 | 0.50 | 0.82 | 0.62 | 0.90 |
| (low) | 1.19 | 0.34 | 0.69 | 0.20 | 0.60 |

Approximate dose for both inoculations:
15 D-3 × 10⁶, 1 × 10⁶ and 3 × 10⁵
15 D(pCMV β) with or without DAP-1 × 10⁶, 5 × 10⁵, 1 × 10⁵
$^A$polymixin B was added to the β-gal protein to chelate any contaminating LPS.

These results indicate that in this model, 15D can successfully delivery pCMVβ DNA. At higher inoculating doses, mice that have been inoculated with 15D(pCMVβ) with or without the addition of DAP are capable of proliferating in response to β-gal. In addition, there was no significant proliferative responses to the carrier at the doses given.

EXAMPLE 9

Mouse Intranasal Response II

Lymphoproliferative and antibody responses directed against the plasmid expressed β-galactosidase were measured after bacterial delivery of plasmid DNA to the nasal tissue of mice. Two intranasal inoculations were administered on days 0 and 28. Four weeks after the last inoculation, splenocytes from mice receiving 15D(pCMVβ) showed lymphoproliferative responses directed against β-galactosidase. Eight to 10 week-old female BALB/c mice (Harlan Sprague Dawley, Indianapolis, Ind.) were sedated by intramuscular injection of a mixture of 0.3 mg xylazine hydrochloride (Rompun; Mobay Corp., Shawnee, Kans.) and 1.0 mg of ketamine hydrochloride (Ketaset; Aveco Company, Fort Dodge, Iowa) in 50 μl of saline. A concentrated bacterial suspension (15 μl) was dropped onto the external nares of each mouse. Mice in groups of 5 to 10 were administered either 10⁶ or 10⁷ viable bacteria on day 0 and 4 weeks. Some groups of mice received inocula of 15D(pCMVβ) supplemented with 50 μg/ml of DAP. Blood for serum analysis was collected 4 weeks after the last inoculation. At that time, spleens were also removed for in vitro determination of lymphoproliferative responses induced by ConA, *E. coli* LPS, heat-killed 2457T, and purified β-galactosidase (Sigma, St. Louis, Mo.). Splenocytes (1×10⁵/well) were cultured in the presence of 5 μg/ml ConA, 2.5 μg/ml *E. coli* LPS, 5 μg/ml heat-killed 2457T, and 2.5 μg/ml β-galactosidase with 10 μg/ml polymixin B (Burroughs Wellcome, Research Triangle Park, N.C.) for 3 days. Levels of proliferation were determined using a Cell Titer 96™ A Q$_{ueous}$ non-radioactive cell proliferation kit (Promega, Madison, Wis.). Reported OD490 values were calculated by subtracting the mean value of unstimulated cells from the mean value of stimulated cells.

Figure 4A:
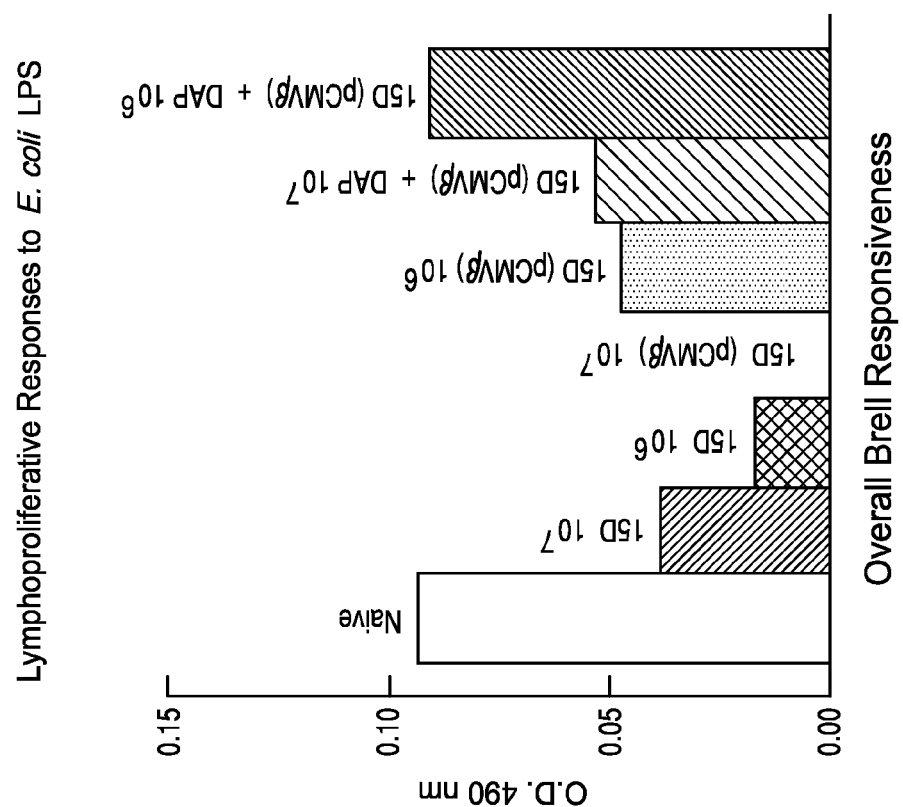
FIG. 4 shows lymphoproliferative responses induced by ConA (FIG. 4A), E. coli LPS (FIG. 4B), heat-killed 2457T (FIG. 4C), and purified β-galactosidase (FIG. 4D) from mice receiving a concentrated bacterial suspension intranasally. Splenocytes (1×10$^5$/well) were cultured in the presence of 5 µg/ml ConA, 2.5 µg/ml E. coli LPS, 5 µg/ml heat-killed 2457T, and 2.5 µg/ml β-galactosidase with 10 µg/ml polymixin B (Burroughs Wellcome, Research Triangle Park, N.C.) for 3 days. Levels of proliferation were determined using a Cell Titer 96™ A Q$_{ueous}$ non-radioactive cell proliferation kit (Promega, Madison, Wis.). Reported OD490 values were calculated by subtracting the mean value of unstimulated cells from the mean value of stimulated cells.
Figure 4B:
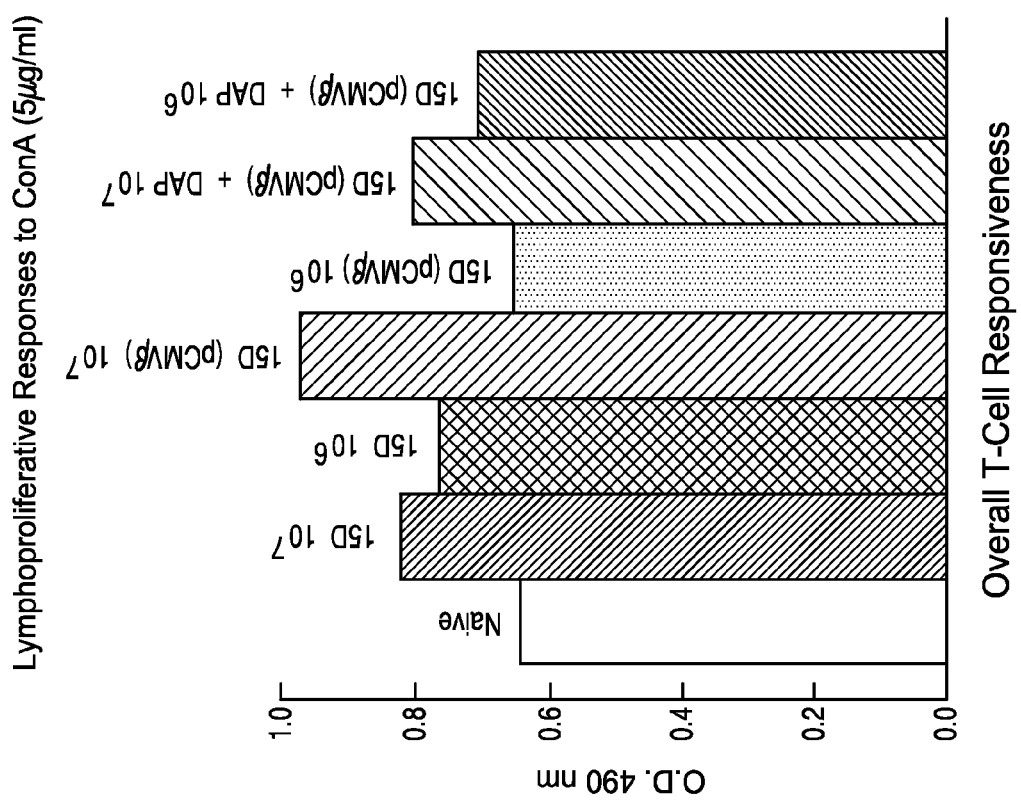
Figures 4C, 4D:
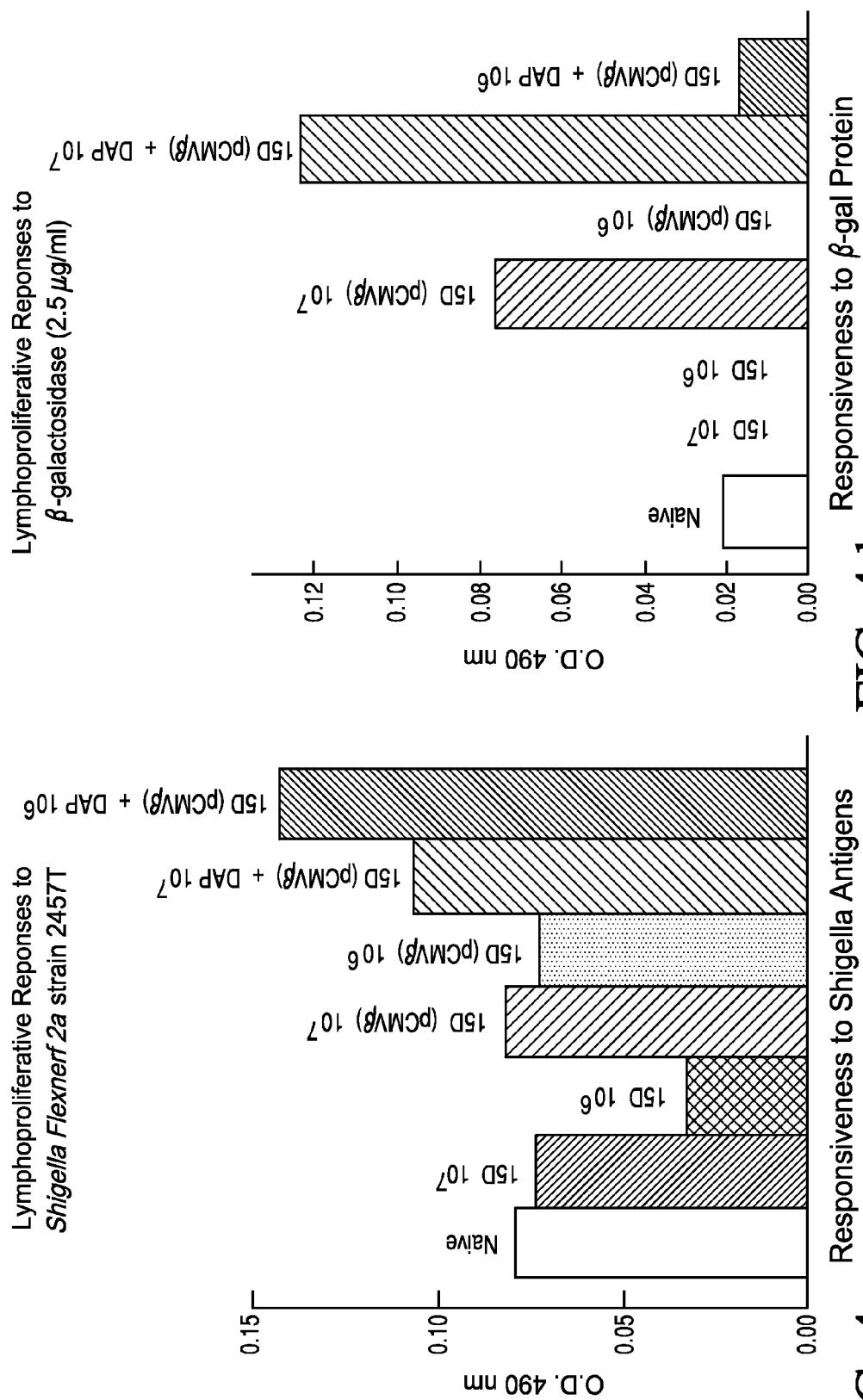
Figure 5:
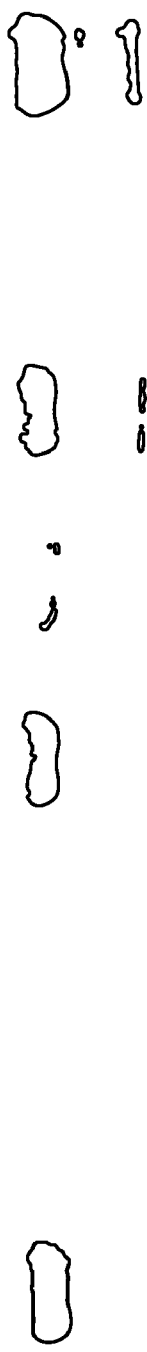
FIG. 5 is a Western showing antibody responses to β-galactosidase of intranasally inoculated mice. Groups of mice were inoculated with either 15D, 15D(pCMVβ), or 15D(pCMVβ) containing 50 µg/ml of DAP. Sera was tested for reactivity to β-galactosidase. Lane A, coomassie stained SDS-PAGE gel. Immunoblot lanes B-G were exposed to 1:50 dilution of pooled sera from mice inoculated with: B, 10$^6$ 15D; C, 10$^7$ 15D; D, 10$^7$ 15D(pCMVβ); E, 10$^6$ 15D (pCMVβ); F, 10$^7$ 15D(pCMVβ)+DAP; and G, 10$^6$ 15D (pCMVβ)+DAP. Immunoblot control lanes; H, 1:10,000 anti-β-galactosidase (Promega); I, 1:50 dilution of pooled sera from saline inoculated mice; and J, 1:500 secondary rabbit anti-mouse conjugated with alkaline phosphatase.

Results indicate that mice inoculated with 15D(pCMVβ) with or without the addition of DAP are capable of proliferating in response to β-galactosidase, up to five-fold higher than controls (FIG. 4D).

EXAMPLE 10

Antibody Responses to β-galactosidase of Intranasally Inoculated Mice

Sera from groups of mice inoculated with either 15D, 15D(pCMVβ), or 15D(pCMVβ) containing 50 μg/ml of DAP were tested for reactivity to β-galactosidase. One microgram of purified β-galactosidase was electrophoresed on 7.5% SDS-polyacrylamide gels. After electrophoresis, gels were electroblotted to nitrocellulose. Casein blocked blots were then sectioned before overnight exposure to pooled sera samples (diluted 1:50 in casein buffer). Bound antibody was detected with a 1:500 dilution of secondary rabbit anti-mouse Ig conjugated with alkaline phosphatase (BMB, Indianapolis, Ind.). Alkaline phosphatase activity was detected by substrates BCIP/NBT (Sigma). Immunoblot analysis revealed antibody responses specific for β-galactosidase in sera samples from mice infected with 15D (pCMV β).

Sera samples were also analyzed by ELISA to determine antibody isotype and IgG subclass using standard methodology. Antibody specific for β-galactosidase was of the IgG isotype with IgG1, IgG2a, and IgG2b subclasses equally represented (Table 7), indicating involvement of both Th1 and Th2 cells.

TABLE 7

ELISA results

| Animals inoculated with: | Anti-β-galactosidase Total IgG Titer: |
|---|---|
| saline | 0 |
| 15 D $10^7$ | 1:100 |
| 15 D $10^6$ | 0 |
| 15 D(pCMV β) $10^7$ | 1:12800 |
| 15 D(pCMV β) $10^6$ | 1:800 |
| 15 D(pCMV β) + DAP $10^7$ | 1:6400 |
| 15 D(pCMV β) + DAP $10^6$ | 0 |

IgG Subclass Typing

| | Anti-β-galactosidase: | | |
|---|---|---|---|
| Animals inoculated with: | IgG1 | IgG2a | IgG2b |
| 15 D(pCMV β) $10^7$ | 1:25600 | 1:25600 | 1:6400 |
| 15 D(pCMV β) $10^6$ | 1:800 | 1:1600 | 1:1600 |
| 15 D(pCMV β) + DAP $10^7$ | 1:3200 | 1:12800 | 1:3200 |

The results presented here represented the first evidence that attenuated bacteria can be used to deliver plasmid DNA to mucosal surfaces with subsequent stimulation of immune responses directed against the plasmid-encoded foreign gene product. This approach to vaccine development should simplify production and delivery of DNA-based vaccines, while expanding the technology to allow stimulation of often desired mucosal immune responses.

We have discovered a novel method for delivering functional DNA inside cells. This method should not be restricted to *Shigella*, since the invasion genes that *Shigella* utilizes can be inserted into other bacteria such as *E. coli* (Sansonetti et al. *Infect. Immun.* (1983) 39:1392). Likewise, other bacteria such as *Listeria* are able to invade cells and break out of the phagocytic vacuole into the cytoplasm (Portnoy and Jones, *Ann. N.Y. Acad. Sci.* (1994) 730:15). Although we have no formal proof that release from the phagocytic vacuole into the cell cytoplasm by the bacteria is essential for DNA delivery, preliminary experiments with *Salmonella typhimurium*, an organism that reaches the cytoplasm only with difficulty, suggests this organism is not an efficient DNA delivery vehicle.

Any bacterial vector DNA delivery system will need to strike a balance between cell invasion with its subsequent reactogenicity and efficiency of delivery. In the case of *Shigella*, the genes responsible for invasion also cause invasion and apoptosis of macrophages followed by inflammation (Zychlinsky et al. *Nature* (1992) 358: 167). We constructed a *Shigella* strain that in the absence of DAP, is unable to survive inside the cell. Determination of the safety of this strain awaits human trials.

The bacterial DNA delivery system which we describe has several advantages for certain applications. Delivery of DNA encoded antigens to the mucosal immune system should permit mucosal immunization simultaneously with multiple antigens that can be directed for class I and/or II presentation, stimulation of Th1 or Th2 help, or secreted maintaining the proper folding and conformational epitopes for IgA and IgG antibody production. Diarrheal diseases such as rotavirus; sexually transmitted diseases such as human immunodeficiency virus, *Neisseria gonorrhoeae*, and human papilloma virus; and gastrointestinal diseases such as the ulcer causing *Helicobacter pylori*, to name a few, may be especially responsive to this approach. Suppression of autoimmunity through manipulation of gut immune tolerance mechanisms has been demonstrated (Sun et al. *Proc. Natl. Acad. Sci. U.S.A.* (1994) 91: 10795), and should also be amenable to this approach.

Perhaps the greatest advantage of bacterial delivery of DNA for vaccination and potential gene therapy/replacement is the ease and acceptability or oral and other forms of mucosal delivery. Likewise, because no DNA purification is required for this type of DNA vaccination, which is really a live, attenuated bacterial vector, vaccines can be produced for the cost of fermentation, lyophilization and packaging. Therefore, this type of vaccination may represent at least in part a solution to the cost and difficulty of current vaccines and those that are being developed.

What is claimed is:

1. A method for delivering an antigen to a cell comprising:

(i) introducing said antigen into an attenuated *Shigella*; and (ii) administering said *Shigella* to said cell.

2. A method for delivering an antigen to a cell according to claim 1, wherein said *Shigella* is *S. flexneri*.

3. A method for delivering an antigen to a cell according to claim 1, wherein said cell is a cell of a mucosal epithelium.

4. A method for delivering an antigen to a cell according to claim 1, wherein said attenuated *Shigella* is further inactivated.

* * * * *

SEQUENCE LISTING

<160> NUMBER OF SEQ ID NOS: 8

<210> SEQ ID NO 1
<211> LENGTH: 1674

<210> SEQ ID NO 1
<211> LENGTH: 1674
<212> TYPE: DNA
<213> ORGANISM: Shigella sp.

<400> SEQUENCE: 1

| | | | | | |
|---|---|---|---|---|---|
| tccataatca | ggatcaataa | aactgctgca | gaaatgattt | cattcataac | tcaaattccc | 60 |
| tgataattgc | cgcggacttt | ctgcgtgcta | acaaagcagg | ataagtcgca | ttactcatgg | 120 |
| cttcgctatc | attgattaat | ttcacttgcg | actttggctg | cttttttgtat | ggtgaaagat | 180 |
| gtgccaagag | gagaccggca | catttataca | gcacacatct | ttgcaggaaa | aaaacgctta | 240 |
| tgaaaaatgt | tggttttatc | ggctggcgcg | gtatggtcgg | ctccgttctc | atgcaacgca | 300 |
| tggttgaaga | gcgcgacttc | gacgccattc | gccctgtctt | cttttttctac | ttctcagctt | 360 |
| ggccaggctg | cgccgtcttt | tggcggaacc | actggcacac | tcaggatgcc | tttgatctgg | 420 |
| aggcgctaaa | ggccctcgat | atcattgtga | cctgtcaggg | cggcgattat | accaacgaaa | 480 |
| tctatccaaa | gcttcgtgaa | agcggatggc | aaggttactg | gattgacgca | gcatcgtctc | 540 |
| tgcgcatgaa | agatgacgcc | atcatcattc | ttgaccccgt | caatcaggac | gtcattaccg | 600 |
| acggattaaa | taatggcatc | aggactttg | ttggcggtaa | ctgtaccgta | agcctgatgt | 660 |
| tgatgtcgtt | gggtggttta | ttcgccaatg | atcttgttga | ttgggtgtcc | gttgcaacct | 720 |
| accaggccgc | ttccggcggt | ggtgcgcgac | atatgcgtga | gttattaacc | cagatgggcc | 780 |
| atctgtatgg | ccatgtggca | gatgaactcg | cgaccccgtc | ctctgctatt | ctcgatatcg | 840 |
| aacgcaaagt | cacaaccta | acccgtagcg | gtgagctgcc | ggtggataac | tttggcgtgc | 900 |
| cgctggcggg | tagcctgatt | ccgtggatcg | acaaacagct | cgataacggt | cagagccgcg | 960 |
| aagagtggaa | agggcaggcg | gaaaccaaca | agatcctcaa | cacatcttcc | gtaattccgg | 1020 |
| tagatggttt | atgtgtgcgt | gtcggggcat | tgcgctgcca | cagccaggca | ttcactatta | 1080 |
| aattgaaaaa | agatgtgtct | attccgaccg | tggaagaact | gctggctgcg | cacaatccgt | 1140 |
| gggcgaaagt | cgttccgaac | gatcgggaaa | tcactatgcg | tgagctaacc | ccagctgccg | 1200 |
| ttaccggcac | gctgaccacg | ccggtaggcc | gcctgcgtaa | gctgaatatg | ggaccagagt | 1260 |
| tcctgtcagc | ctttaccgtg | ggcgaccagc | tgctgtgggg | ggccgcggag | ccgctgcgtc | 1320 |
| ggatgcttcg | tcaactggcg | taatctttat | tcattaaatc | tggggcgcga | tgccgcccct | 1380 |
| gttagtgcgt | aatacaggag | taagcgcaga | tgtttcatga | tttaccggga | gttaaataga | 1440 |
| gcattggcta | ttctttaagg | gtggctgaat | acatgagtat | tcacagcctt | acctgaagtg | 1500 |
| aggacgacgc | agagaggatg | cacagagtgc | tgcgccgttc | aggtcaaaaa | aatgtcacaa | 1560 |
| ccagaagtca | aaaatccaat | tggatggggt | gacacaataa | aacaggaaga | caagcatgtc | 1620 |
| cgatcgtatc | gatagagacg | tgattaacgc | gctaattgca | ggccatttg | cgga | 1674 |

<210> SEQ ID NO 2
<211> LENGTH: 1121
<212> TYPE: DNA
<213> ORGANISM: Shigella sp.
<220> FEATURE:
<221> NAME/KEY: misc_feature
<222> LOCATION: (439)..(991)
<223> OTHER INFORMATION: The E.coli asd gene coding for b-aspartic
      semialdehyde dehydrogenase identified in Seq. ID No. 1 was
      modified by deleting 553 base pairs from position 439 to 991.

<400> SEQUENCE: 2

| | | | | | |
|---|---|---|---|---|---|
| tccataatca | ggatcaataa | aactgctgca | gaaatgattt | cattcataac | tcaaattccc | 60 |
| tgataattgc | cgcggacttt | ctgcgtgcta | acaaagcagg | ataagtcgca | ttactcatgg | 120 |

```
cttcgctatc attgattaat ttcacttgcg actttggctg cttttttgtat ggtgaaagat    180 gtgccaagag gagaccggca catttataca gcacacatct ttgcaggaaa aaaacgctta    240
tgaaaaatgt tggttttatc ggctggcgcg gtatggtcgg ctccgttctc atgcaacgca    300
tggttgaaga gcgcgacttc gacgccattc gccctgtctt cttttctact tctcagcttg    360
gccaggctgc gccgtctttt ggcggaacca ctggcacact tcaggatgcc tttgatctgg    420
aggcgctaaa ggccctcgga tcctcaacac atcttccgta attccggtag atggtttatg    480
tgtgcgtgtc ggggcattgc gctgccacag ccaggcattc actattaaat tgaaaaaga    540 tgtgtctatt ccgaccgtgg aagaactgct ggctgcgcac aatccgtggg cgaaagtcgt    600
tccgaacgat cgggaaatca ctatgcgtga gctaacccca gctgccgtta ccggcacgct    660
gaccacgccg gtaggccgcc tgcgtaagct gaatatggga ccagagttcc tgtcagcctt    720
taccgtgggc gaccagctgc tgtgggggggc cgcggagccg ctgcgtcgga tgcttcgtca    780
actggcgtaa tctttattca ttaaatctgg ggcgcgatgc cgccctgtt agtgcgtaat    840 acaggagtaa gcgcagatgt tcatgatttt accgggagtt aaatagagca ttggctattc    900
tttaagggtg gctgaataca tgagtattca cagccttacc tgaagtgagg acgacgcaga    960
gaggatgcac agagtgctgc gccgttcagg tcaaaaaaat gtcacaacca gaagtcaaaa   1020
atccaattgg atggggtgac acaataaaac aggaagacaa gcatgtccga tcgtatcgat   1080
agagacgtga ttaacgcgct aattgcaggc cattttgcgg a                        1121

<210> SEQ ID NO 3
<211> LENGTH: 22
<212> TYPE: DNA
<213> ORGANISM: Shigella sp.

<400> SEQUENCE: 3
agatctccct gataattgcc gc                                               22

<210> SEQ ID NO 4
<211> LENGTH: 26
<212> TYPE: DNA
<213> ORGANISM: Shigella sp.

<400> SEQUENCE: 4
agatctcgct tactcctgta ttacgc                                           26

<210> SEQ ID NO 5
<211> LENGTH: 20
<212> TYPE: DNA
<213> ORGANISM: Shigella sp.

<400> SEQUENCE: 5
cgagggcctt tagcgcctcc                                                  20

<210> SEQ ID NO 6
<211> LENGTH: 20
<212> TYPE: DNA
<213> ORGANISM: Shigella sp.

<400> SEQUENCE: 6
gatcctcaac acatcttccg                                                  20

<210> SEQ ID NO 7
<211> LENGTH: 22
<212> TYPE: DNA
<213> ORGANISM: Shigella sp.
```

-continued

```
<400> SEQUENCE: 7
gagctcccct gataattgcc gc                                           22

<210> SEQ ID NO 8
<211> LENGTH: 26
<212> TYPE: DNA
<213> ORGANISM: Shigella sp.

<400> SEQUENCE: 8
gtcgaccgct tactcctgta ttacgc                                       26
```